US011331443B2

(12) United States Patent
Weigensberg et al.

(10) Patent No.: US 11,331,443 B2
(45) Date of Patent: *May 17, 2022

(54) TOPOGRAPHY APPARATUS FOR ELECTRONIC VAPING DEVICE

(71) Applicant: Altria Client Services LLC, Richmond, VA (US)

(72) Inventors: Isaac Weigensberg, Richmond, VA (US); Yuval Malka, Richmond, VA (US); Boris Bessarabov, Richmond, VA (US); David Rubli, Revava (IL); Moshe Eliyahu, Beit Shemesh (IL); Phillip Diana, Richmond, VA (US); Alex Malamud, Jerusalem (IL)

(73) Assignee: Altria Client Services LLC, Richmond, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/142,579

(22) Filed: Jan. 6, 2021

(65) Prior Publication Data

US 2021/0153563 A1  May 27, 2021

Related U.S. Application Data

(63) Continuation of application No. 15/604,500, filed on May 24, 2017, now Pat. No. 10,897,930.

(51) Int. Cl.
*A61M 15/06* (2006.01)
*A61M 11/04* (2006.01)
(Continued)

(52) U.S. Cl.
CPC ............ *A61M 15/06* (2013.01); *A24F 40/40* (2020.01); *A24F 40/51* (2020.01); *A24F 40/65* (2020.01);
(Continued)

(58) Field of Classification Search
None
See application file for complete search history.

(56) References Cited

U.S. PATENT DOCUMENTS 6,814,083 B2  11/2004  Likness et al.
9,289,014 B2   3/2016  Tucker et al.
(Continued)

FOREIGN PATENT DOCUMENTS

CN   204169050 U   2/2015
CN   204670381 U   9/2015
(Continued)

OTHER PUBLICATIONS

R.J. Robinson et al., "electronic Cigarette Topography in the Natural Environment", PLOS ONE, DOI:10.1371/journal.pone.0129296, Jun. 8, 2015.
(Continued)

*Primary Examiner* — Roy Y Yi
(74) *Attorney, Agent, or Firm* — Harness, Dickey & Pierce, P.L.C.

(57) ABSTRACT

A topography apparatus may be coupled to an e-vaping device, within an interior defined by a housing of the e-vaping device, such that the topography apparatus may be coupled to an e-vaping device that may generate vapor independently of the topography apparatus. The topography apparatus may generate and communicate vapor topography data associated with vapor generation by the e-vaping device without altering an external appearance or vapor-generation performance of the e-vaping device. The topography apparatus may be detachably coupled to the interior of the e-vaping device. The topography apparatus includes an interface assembly configured to couple with a power supply, control circuitry, and/or sensor of the e-vaping device. Such coupling may include coupling with internal power or communication conduits of the e-vaping device, such that
(Continued)

the topography apparatus taps into power and/or communication lines of the e-vaping device without requiring modification of the circuitry of the e-vaping device.

17 Claims, 7 Drawing Sheets

(51) Int. Cl.
*A24F 40/65* (2020.01)
*A24F 40/40* (2020.01)
*A24F 40/51* (2020.01)
*A24F 40/10* (2020.01)
*H04W 4/80* (2018.01)

(52) U.S. Cl.
CPC ............ *A61M 11/042* (2014.02); *A24F 40/10* (2020.01); *A61M 2205/3569* (2013.01); *A61M 2205/3592* (2013.01); *A61M 2205/50* (2013.01); *A61M 2205/8206* (2013.01); *A61M 2205/8237* (2013.01); *H04W 4/80* (2018.02)

(56) References Cited

U.S. PATENT DOCUMENTS

| | | |
|---|---|---|
| 10,897,930 B2 * | 1/2021 | Weigensberg .......... A24F 40/51 |
| 2004/0030508 A1 | 2/2004 | Likness et al. |
| 2006/0099554 A1 | 5/2006 | Frost |
| 2013/0192623 A1 | 8/2013 | Tucker et al. |
| 2013/0284192 A1 | 10/2013 | Peleg et al. |
| 2014/0174459 A1 | 6/2014 | Burstyn |
| 2014/0278250 A1 | 9/2014 | Smith et al. |
| 2014/0278258 A1 | 9/2014 | Shafer |
| 2014/0305450 A1 | 10/2014 | Xiang |
| 2015/0327596 A1 | 11/2015 | Alarcon et al. |
| 2016/0255878 A1 | 9/2016 | Huang et al. |
| 2016/0278435 A1 | 9/2016 | Choukroun et al. |
| 2016/0309785 A1 | 10/2016 | Holtz |
| 2016/0309786 A1 | 10/2016 | Holtz et al. |
| 2016/0309787 A1 | 10/2016 | Hawes et al. |
| 2017/0013883 A1 | 1/2017 | Han et al. |
| 2017/0020195 A1 | 1/2017 | Cameron |
| 2017/0046357 A1 | 2/2017 | Cameron |
| 2017/0071262 A1 | 3/2017 | Liu |
| 2017/0092106 A1 | 3/2017 | Cameron |
| 2017/0325502 A1 | 11/2017 | Nelson et al. |

FOREIGN PATENT DOCUMENTS

| | | |
|---|---|---|
| WO | WO-2016/019550 A1 | 2/2016 |
| WO | WO-2016/029464 A1 | 3/2016 |
| WO | WO-2016/079533 A1 | 5/2016 |
| WO | WO-2017037457 A1 | 3/2017 |

OTHER PUBLICATIONS

Tory Spindle, Examination of Electronic Cigarette User Puff Topography: The Effect of a Mouthpiece-Based Topography Measurement Device on Plasma Nicotine and Subjective Effects, Virginia Commonwealth University, VCU Scholars Compass. 2015.

Rachel Z. Behar, "Puffing Topography and Nicotne Intake of Electronic Cigarette Users", PLOS ONE/DOI,10,1371, Feb. 9, 2015.

International Search Report and Written Opinion thereof dated Aug. 1, 2018 for corresponding International Application No. PCT/EP2018/063736.

Written Opinion of the International Preliminary Examining Authority dated Apr. 10, 2019 for corresponding International Application No. PCT/EP2018/063736.

International Preliminary Report on Patentability dated Jun. 14, 2019 for corresponding International Application No. PCT/EP2018/063736.

Cunningham et al., "Development, Validation and Application of a Device to measure E-cigarette Users' Putting Topography", Scientific Reports, 2016 (Year: 2016).

* cited by examiner

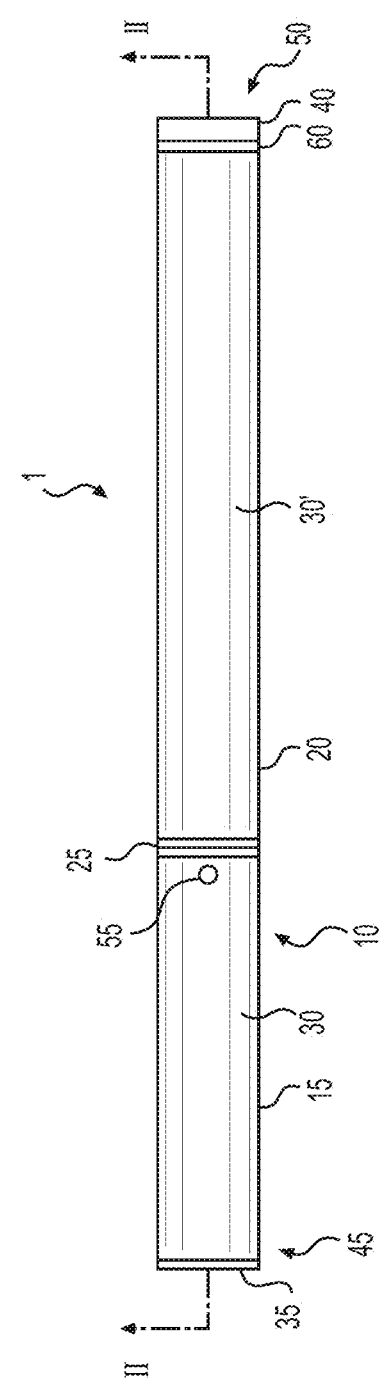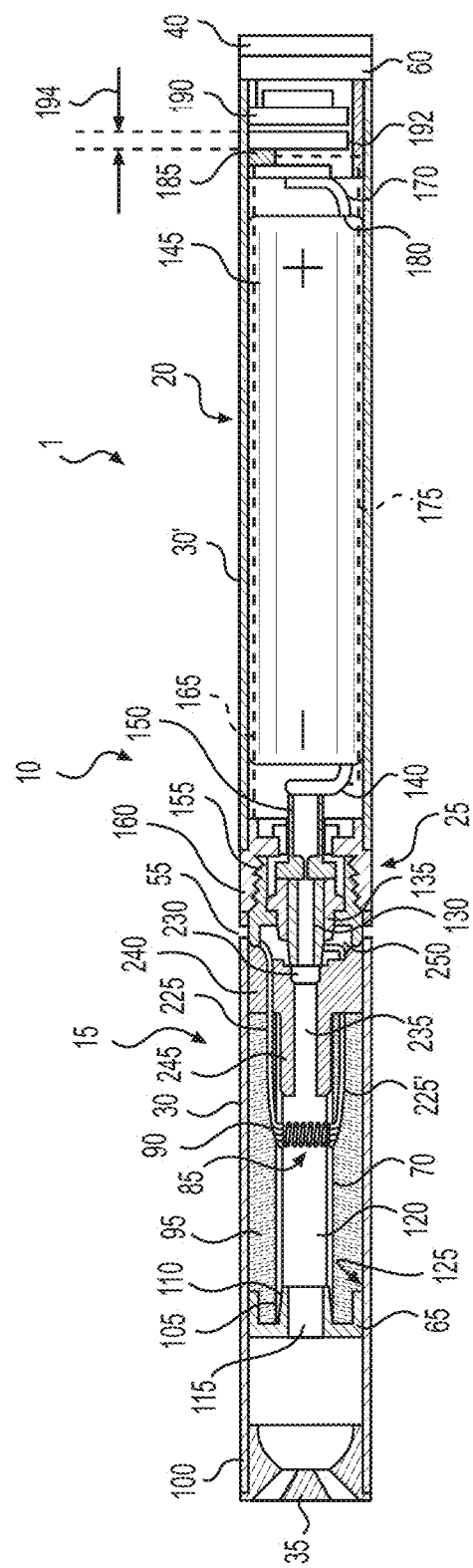

TOPOGRAPHY APPARATUS FOR ELECTRONIC VAPING DEVICE

CROSS-REFERENCE TO RELATED APPLICATIONS

This is a continuation application of U.S. application Ser. No. 15/604,500, filed May 24, 2017, the entire contents of which are incorporated herein by reference.

BACKGROUND

Field

The present disclosure relates generally to electronic vaping devices (also referred to herein as simply "e-vaping devices") and more particularly to generating vapor topography data (also referred to herein as simply "topography data") associated with the generation of vapor by e-vaping devices.

Description of Related Art

An e-vaping device includes a heater element which vaporizes a pre-vapor formulation to produce a "vapor." Such a vapor may be referred to herein as a "generated vapor."

The e-vaping device includes a power supply, such as a rechargeable battery, arranged in the device. The battery is electrically connected to the heater, such that the heater heats to a temperature sufficient to convert a pre-vapor formulation to a vapor. The vapor exits the e-vaping device through an outlet-end insert including at least one outlet.

SUMMARY

According to some example embodiments, a topography apparatus may be configured to be coupled to an e-vaping device within an interior space that is at least partially defined by a housing of the e-vaping device. The topography apparatus may include an interface assembly configured to communicatively couple with a power supply of the e-vaping device, a memory storing a program of instructions, a processor, and a communication interface. The processor may be configured to execute the program of instructions to generate vapor topography data based on processing a signal received from an element included within the interior space of the e-vaping device, where the vapor topography data indicates a physical characteristic of a pattern of vapor generation by the e-vaping device. The communication interface may be configured to communicate the vapor topography data to an external device, the external device separately located in relation to the e-vaping device and the topography apparatus.

The topography apparatus may be configured to be detachably coupled with the e-vaping device.

The communication interface may be configured to transmit the vapor topography data to the external device via a wireless network connection.

The communication interface may be configured to communicatively couple with a power charging interface of the e-vaping device, such that the communication interface is configured to communicate the vapor topography data to the external device via the power charging interface.

The topography apparatus may further include a topography apparatus sensor that may be configured to generate topography sensor data based on an operation of the e-vaping device. The processor may be configured to execute the program of instructions to generate the vapor topography data based on processing the topography sensor data generated by the topography apparatus sensor.

The vapor topography data may indicate at least one of a time stamp associated with a generation of vapor by the e-vaping device, a voltage output of the power supply of the e-vaping device in association with generation of vapor by the e-vaping device, an amount of vapor generated by the e-vaping device, a flow rate of vapor generated by the e-vaping device, or a presence of a volatile organic compound (VOC) in the vapor generated by the e-vaping device.

The interface assembly may be configured to couple with a communication conduit of the e-vaping device, the communication conduit communicatively coupling control circuitry of the e-vaping device to the power supply of the e-vaping device, such that the topography apparatus is communicatively coupled to the power supply via the interface assembly and the communication conduit.

The interface assembly may be configured to communicatively couple with a communication conduit of the e-vaping device, the communication conduit communicatively coupling control circuitry of the e-vaping device to a sensor of the e-vaping device, such that the processor is configured to execute the program of instructions to generate vapor topography data based on processing sensor data received from the sensor of the e-vaping device.

The interface assembly may be configured to communicatively couple with control circuitry of the e-vaping device, such that the processor is configured to execute the program of instructions to generate control signals to control the control circuitry based on generating the vapor topography data.

According to some example embodiments, an e-vaping device may include an e-vaping device configured to generate a vapor and a topography apparatus coupled with the e-vaping device. The e-vaping device may include a vaporizer assembly configured to generate the vapor based on heating a pre-vapor formulation and a power supply section configured to supply electrical power to the vaporizer assembly to cause the vaporizer assembly to generate the vapor. The power supply section may further include control circuitry configured to control the supply of electrical power to the vaporizer assembly, and a housing encompassing the power supply section. The topography apparatus may be coupled with the e-vaping device within an interior space at least partially defined by the housing. The topography apparatus may be configured to generate vapor topography data associated with the vaporizer assembly. The vapor topography data may indicate a physical characteristic of a pattern of vapor generation by the vaporizer assembly. The topography apparatus may include an interface assembly configured to communicatively couple with the power supply section, a memory storing a program of instructions, a processor, and a communication interface. The processor may be configured to execute the program of instructions to generate vapor topography data based on processing a signal received from an element included within the interior space of the e-vaping device. The communication interface may be configured to communicate the vapor topography data to an external device, the external device separately located in relation to the e-vaping device and the topography apparatus. The e-vaping device may be configured to generate vapor independently of the topography apparatus being coupled with the e-vaping device.

The topography apparatus may be configured to be detachably coupled with the e-vaping device.

The communication interface may be configured to transmit the vapor topography data to the external device via a wireless network connection.

The communication interface may be configured to communicatively couple with a power charging interface of the e-vaping device, such that the communication interface is configured to communicate the vapor topography data to the external device via the power charging interface.

The topography apparatus may further include a topography apparatus sensor, the topography apparatus sensor configured to generate topography sensor data based on an operation of the e-vaping device. The processor may be configured to execute the program of instructions to generate the vapor topography data based on processing the topography sensor data generated by the topography apparatus sensor.

The vapor topography data may indicate at least one of a time stamp associated with a generation of vapor by the e-vaping device, a voltage output of a power supply of the e-vaping device in association with generation of vapor by the e-vaping device, an amount of vapor generated by the e-vaping device, a flow rate of vapor generated by the e-vaping device, or a presence of a volatile organic compound (VOC) in the vapor generated by the e-vaping device.

The interface assembly may be configured to couple with a communication conduit of the e-vaping device, the communication conduit communicatively coupling control circuitry of the e-vaping device to a power supply of the e-vaping device, such that the topography apparatus is communicatively coupled to the power supply via the interface assembly and the communication conduit.

The interface assembly may be configured to communicatively couple with a communication conduit of the e-vaping device, the communication conduit communicatively coupling control circuitry of the e-vaping device to a sensor of the e-vaping device, such that the processor is configured to execute the program of instructions to generate vapor topography data based on processing sensor data received from the sensor of the e-vaping device.

The interface assembly may be configured to communicatively couple with control circuitry of the e-vaping device, such that the processor is configured to execute the program of instructions to generate control signals to control the control circuitry based on generating the vapor topography data.

According to some example embodiments, a method may include coupling a vaporizer assembly to a power supply section to form an e-vaping device configured to generate a vapor and coupling a topography apparatus to the e-vaping device within an interior defined by a housing of the e-vaping device, such that the e-vaping device is configured to generate the vapor independently of the topography apparatus and the topography apparatus is configured to generate vapor topography data associated with the e-vaping device. The vapor topography data may indicate a physical characteristic of a pattern of vapor generation by the e-vaping device. The topography apparatus may be further configured to communicate the vapor topography data to an external device. The external device may be separately located in relation to the e-vaping device and the topography apparatus.

The topography apparatus may be configured to be detachably coupled to the interior of the e-vaping device, and the method may further include decoupling the topography apparatus from the e-vaping device such that the e-vaping device is configured to generate vapor in an absence of the topography apparatus.

The topography apparatus may include a topography apparatus sensor. The topography apparatus sensor may be configured to generate topography sensor data based on an operation of the e-vaping device. The topography apparatus may further be configured to generate the vapor topography data based on processing sensor data generated by the topography apparatus sensor. The vapor topography data may indicate at least one of a time stamp associated with a generation of vapor by the e-vaping device, a voltage output of a power supply of the e-vaping device in association with generation of vapor by the e-vaping device, an amount of vapor generated by the e-vaping device, a flow rate of vapor generated by the e-vaping device, or a presence of a volatile organic compound (VOC) in the vapor generated by the e-vaping device.

According to some example embodiments, a method may include receiving, at a topography apparatus coupled to an e-vaping device within an interior defined by a housing of the e-vaping device, a signal from an element included within the interior of the e-vaping device, the signal being received based on a generation of vapor by the e-vaping device. The method may include generating vapor topography data based on processing the signal, the vapor topography data indicating a physical characteristic of a pattern of vapor generation by the e-vaping device. The method may include communicating the vapor topography data to an external device. The external device may be separately located in relation to the e-vaping device and the topography apparatus.

The vapor topography data may indicate at least one of a time stamp associated with a generation of vapor by the e-vaping device, a voltage output of a power supply of the e-vaping device in association with generation of vapor by the e-vaping device, an amount of vapor generated by the e-vaping device, a flow rate of vapor generated by the e-vaping device, or a volatile organic compound (VOC) in the vapor generated by the e-vaping device.

The communicating may include transmitting the vapor topography data to the external device via a wireless network connection.

The signal may be received from a topography apparatus sensor included in the topography apparatus, separately from a sensor of the e-vaping device.

BRIEF DESCRIPTION OF THE DRAWINGS

The various features and advantages of the non-limiting embodiments herein may become more apparent upon review of the detailed description in conjunction with the accompanying drawings. The accompanying drawings are merely provided for illustrative purposes and should not be interpreted to limit the scope of the claims. The accompanying drawings are not to be considered as drawn to scale unless explicitly noted. For purposes of clarity, various dimensions of the drawings may have been exaggerated.

FIG. 1 is a side view of an e-vaping device according to some example embodiments.

FIG. 2 is a cross-sectional view along line II-II of the e-vaping device of FIG. 1.

DETAILED DESCRIPTION OF EXAMPLE EMBODIMENTS

Figure 3A:
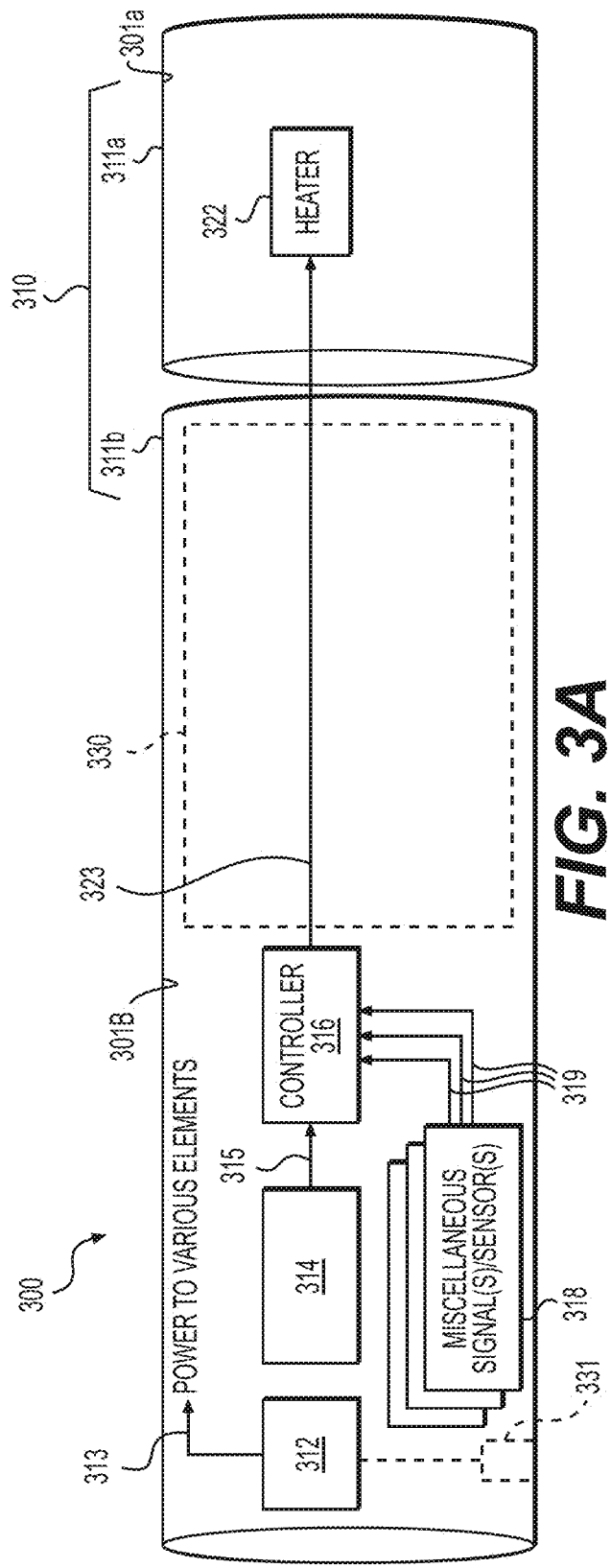
FIG. 3A is a schematic of an e-vaping device in which a topography apparatus is absent, according to some example embodiments.

Some detailed example embodiments are disclosed herein. However, specific structural and functional details disclosed herein are merely representative for purposes of describing example embodiments. Example embodiments may, however, be embodied in many alternate forms and should not be construed as limited to only the example embodiments set forth herein.

Accordingly, while example embodiments are capable of various modifications and alternative forms, example embodiments thereof are shown by way of example in the drawings and will herein be described in detail. It should be understood, however, that there is no intent to limit example embodiments to the particular forms disclosed, but to the contrary, example embodiments are to cover all modifications, equivalents, and alternatives falling within the scope of example embodiments. Like numbers refer to like elements throughout the description of the figures.

It should be understood that when an element or layer is referred to as being "on," "connected to," "coupled to," or "covering" another element or layer, it may be directly on, connected to, coupled to, or covering the other element or layer or intervening elements or layers may be present. In contrast, when an element is referred to as being "directly on," "directly connected to," or "directly coupled to" another element or layer, there are no intervening elements or layers present. Like numbers refer to like elements throughout the specification. As used herein, the term "and/or" includes any and all combinations of one or more of the associated listed items.

It should be understood that, although the terms first, second, third, etc. may be used herein to describe various elements, components, regions, layers and/or sections, these elements, components, regions, layers, and/or sections should not be limited by these terms. These terms are only used to distinguish one element, component, region, layer, or section from another region, layer, or section. Thus, a first element, component, region, layer, or section discussed below could be termed a second element, component, region, layer, or section without departing from the teachings of example embodiments.

Spatially relative terms (e.g., "beneath," "below," "lower," "above," "upper," and the like) may be used herein for ease of description to describe one element or feature's relationship to another element(s) or feature(s) as illustrated in the figures. It should be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" may encompass both an orientation of above and below. The device may be otherwise oriented (rotated 90 degrees or at other orientations) and the spatially relative descriptors used herein interpreted accordingly.

The terminology used herein is for the purpose of describing various example embodiments only and is not intended to be limiting of example embodiments. As used herein, the singular forms "a," "an," and "the" are intended to include the plural forms as well, unless the context clearly indicates otherwise. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

Example embodiments are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments should not be construed as limited to the shapes of regions illustrated herein but are to include deviations in shapes that result, for example, from manufacturing.

Unless otherwise defined, all terms (including technical and scientific terms) used herein have the same meaning as commonly understood by one of ordinary skill in the art to which example embodiments belong. It will be further understood that terms, including those defined in commonly used dictionaries, should be interpreted as having a meaning that is consistent with their meaning in the context of the relevant art and will not be interpreted in an idealized or overly formal sense unless expressly so defined herein.

FIG. 1 is a side view of an e-vaping device assembly 1 according to some example embodiments. FIG. 2 is a cross-sectional view along line II-II' of the e-vaping device assembly 1 of FIG. 1.

As shown in FIGS. 1-2, an e-vaping device assembly 1 may include an e-vaping device 10 ("electronic vaping device") and a topography apparatus 192. As shown in FIGS. 1-2 and as described further below, the topography apparatus 192 may be coupled to the electronic vaping device (e-vaping device 10), within an interior at least partially defined by a housing of the e-vaping device 10, to form the e-vaping device assembly 1 that is configured to generate vapor topography data associated with vapor generation by the e-vaping device. As a result, the e-vaping device 10 is configured to generate vapor independently of the topography apparatus 192, the topography apparatus 192 may be coupled to the e-vaping device 10 without affecting a structural configuration of the elements of the e-vaping device 10 configured to enable vapor generation thereby, without noticeably affecting vapor generation performance of the e-vaping device 10, and without altering an external appearance of the e-vaping device 10.

As described herein, "noticeably" affecting vapor generation performance of the e-vaping device 10 may be understood to mean causing a change in the operational limits of the e-vaping device 10 with regard to vapor generation that exceeds a threshold amount of change from operational limits of the e-vaping device 10 in the absence of the topography apparatus 192. Such, a threshold value associated with "noticeably" affecting vapor generation performance may be 1%. For example, a topography apparatus 192 that, by virtue of being coupled to the e-vaping device 10, causes the amount of vapor generated by the e-vaping device 10 during an instance of vapor generation thereby to decrease by an amount that represents a proportional change that is equal to or less than 1% may be understood to not noticeably affect vapor generation performance of the e-vaping device 10. In another example, a topography apparatus 192 that, by virtue of being coupled to the e-vaping device 10, causes the amount of vapor generated by the e-vaping device 10 during an instance of vapor generation thereby to decrease by an amount that represents a proportional change that is greater than 1% may be understood to noticeably affect vapor generation performance of the e-vaping device 10.

As a result, the topography apparatus 192 enables an e-vaping device 10 that is not configured to generate vapor topography data to be modified, through coupling of the topography apparatus 192 thereto, without noticeably altering the pre-existing elements of the e-vaping device 10. As a result, the capabilities of the e-vaping device assembly that includes the e-vaping device 10 and the coupled topography apparatus 192 are improved over the capabilities of the e-vaping device 10 alone, without reducing or noticeably altering the capabilities of the e-vaping device 10 alone.

In some example embodiments, as shown in FIG. 1, an electronic vaping device (e-vaping device) 10 may include a replaceable cartridge (or first section) 15 and a reusable battery section (or second section) 20, which may be coupled together at a threaded connector 25. It should be appreciated that the connector 25 may be any type of connector, such as a snug-fit, detent, clamp, bayonet, and/or clasp. An air inlet 55 extends through a portion of the connector 25.

In some example embodiments, the connector 25 may be the connector described in U.S. application Ser. No. 15/154,439, filed May 13, 2016 and published as U.S. Patent Application Publication No. 2017/0325502, the entire contents of which is incorporated herein by reference thereto. As described in U.S. application Ser. No. 15/154,439, the connector 25 may be formed by a deep drawn process.

In some example embodiments, the first section 15 may include a first housing 30 and the second section 20 may include a second housing 30'. The e-vaping device 10 includes an outlet-end insert 35 at a first end 45.

As described further below, the first housing 30 and the second housing 30' may each at least partially define an interior space of at least a portion of the e-vaping device 10. As shown in FIG. 2, for example, the second housing 30' at least partially defines an interior space 194 of the e-vaping device 10.

As further shown in FIG. 2, a topography apparatus 192 may be coupled with one or more elements of the e-vaping device 10, within an interior space (e.g., interior space 194) defined by one or more of the housings (e.g., first housing 30 and second housing 30') of the e-vaping device 10, such that the one or more housings cover the topography apparatus 192 from external view. As a result, an e-vaping device 10 that is coupled to the topography apparatus 192 may be externally indistinguishable (e.g., have an indistinguishable visual appearance) in relation to an e-vaping device 10 that is not coupled to the topography apparatus 192.

In some example embodiments, the first housing 30 and the second housing 30' may have a generally cylindrical cross-section. In some example embodiments, the first housing 30 and the second housing 30' may have a generally triangular cross-section along one or more of the first section 15 and the second section 20. Furthermore, the first housing 30 and the second housing 30' may have the same or different cross-section shape, or the same or different size. As discussed herein, the first housing 30 and the second housing 30' may also be referred to as outer or main housings.

As described further below with regard to FIG. 2, each housing, of the first housing 30 and the second housing 30', may define an interior ("interior space") of at least a portion of the e-vaping device 10 and in which one or more elements of the e-vaping device 10 may be included.

In some example embodiments, the e-vaping device 10 may include an end cap 40 at a second end 50 of the e-vaping device 10. The second end 50 may be referred to herein as a "tip end" of the e-vaping device 10. The e-vaping device 10 also includes a light 60 between the end cap 40 and the first end 45 of the e-vaping device 10. The first end 45 of the e-vaping device 10 may be referred to herein as an "outlet end" of the e-vaping device 10.

In some example embodiments, as shown in FIG. 2, the first section 15 may include a reservoir 95 configured to store a pre-vapor formulation and a vaporizer 80 (also referred to herein as a "vaporizer assembly") that may vaporize the pre-vapor formulation to form a generated vapor. Forming a generated vapor may be referred to herein as "generating a vapor," "vapor generation," etc. Vaporizing the pre-vapor formulation may include heating the pre-vapor formulation to cause the pre-vapor formulation to vaporize.

The vaporizer 80 includes a heating element 85 and a wick 90. A heating element may be referred to interchangeably herein as a "heater." The wick 90 may draw the pre-vapor formulation from the reservoir 95. The e-vaping device 10 may include the features set forth in U.S. Patent Application Publication No. 2013/0192623 to Tucker et al. filed Jan. 31, 2013 and/or features set forth in U.S. patent application Ser. No. 15/135,930 to Holtz et al. filed Apr. 22, 2016 and published as U.S. Patent Application Publication No. 2016/0309786, the entire contents of each of which are incorporated herein by reference thereto. In some example embodiments, the e-vaping device may include the features set forth in U.S. patent application Ser. No. 15/135,923 filed Apr. 22, 2016 and published as U.S. Patent Application Publication No. 2016/0309785, and/or U.S. Pat. No. 9,289,014 issued Mar. 22, 2016, the entire contents of each of which is incorporated herein by this reference thereto.

In some example embodiments, the pre-vapor formulation is a material or combination of materials that may be transformed into a vapor ("generated vapor"). For example, the pre-vapor formulation may be a liquid, solid and/or gel formulation including, but not limited to, water, beads, solvents, active ingredients, ethanol, plant extracts, natural or artificial flavors, and/or vapor formers such as glycerin and propylene glycol.

In some example embodiments, the first section 15 may include the housing 30 extending in a longitudinal direction and an inner tube (or chimney) 70 coaxially positioned within the housing 30.

In some example embodiments, a first connector piece 155 may include a male threaded section for effecting the connection between the first section 15 and the second section 20.

At an upstream end portion of the inner tube 70, a nose portion 245 of a gasket (or seal) 240 may be fitted into the inner tube 70; and an outer perimeter of the gasket 240 may provide a seal with an interior surface of the housing 30. The gasket 240 may also include a central, longitudinal air passage 235 in fluid communication with the inner tube 70 to define an inner passage (also referred to as a central channel or central inner passage) 120. A transverse channel 230 at a backside portion of the gasket 240 may intersect and communicate with the air passage 235 of the gasket 240. This transverse channel 230 assures communication between the air passage 235 and a space 250 defined between the gasket 240 and the first connector piece 155.

In some example embodiments, the first connector piece 155 may include a male threaded section for effecting the connection between the first section 15 and the second section 20.

In some example embodiments, at least two air inlets 55 may be included in the housing 30. In some example embodiments, a single air inlet 55 may be included in the housing 30. Such arrangement allows for placement of the air inlet 55 close to the connector 25 without occlusion by the presence of the first connector piece 155. This arrangement may also reinforce the area of air inlets 55 to facilitate precise drilling of the air inlets 55.

In some example embodiments, the air inlets 55 may be provided in the connector 25 instead of in the housing 30. In some example embodiments, the connector 25 may not include threaded portions.

In some example embodiments, the at least one air inlet 55 may be formed in the housing 30, adjacent the connector 25 to minimize the chance of an adult vaper's fingers occluding one of the ports and to control the resistance-to-draw (RTD) during vaping. In some example embodiments, the air inlet 55 may be machined into the housing 30 with precision tooling such that their diameters are closely controlled and replicated from one e-vaping device 10 to the next during manufacture.

In some example embodiments, the air inlets 55 may be sized and configured such that the e-vaping device 10 has a resistance-to-draw (RTD) in the range of from about 60 mm $H_2O$ to about 150 mm $H_2O$.

In some example embodiments, a nose portion 110 of a gasket 65 may be fitted into a first end portion 105 of the inner tube 70. An outer perimeter of the gasket 65 may provide a substantially tight seal with an interior surface 125 of the housing 30. The gasket 65 may include a central channel 115 disposed between the inner passage 120 of the inner tube 70 and the interior of the outlet-end insert 35, which may transport the vapor from the inner passage 120 to the outlet-end insert 35. The outlet-end insert 35 includes at least two outlets 100, which may be located off-axis from the longitudinal axis of the e-vaping device 10. The outlets 100 may be angled outwardly in relation to the longitudinal axis of the e-vaping device 10. The outlets 100 may be substantially uniformly (e.g., uniformly within manufacturing tolerances and/or material tolerances) distributed about the perimeter of the outlet-end insert 35 so as to substantially uniformly distribute vapor.

In some example embodiments, the space defined between the gasket 65, the gasket 240, the housing 30, and the inner tube 70 may establish the confines of the reservoir 95. The reservoir 95 may contain a pre-vapor formulation, and optionally a storage medium (not shown) configured to store the pre-vapor formulation therein. The storage medium may include a winding of cotton gauze or other fibrous material about the inner tube 70.

In some example embodiments, the reservoir 95 may at least partially surround the inner passage 120. Thus, the reservoir 95 may at least partially surround the inner passage 120. The heating element 85 may extend transversely across the inner passage 120 between opposing portions of the reservoir 95. In some example embodiments, the heating element 85 may extend parallel to a longitudinal axis of the inner passage 120.

In some example embodiments, the reservoir 95 may be sized and configured to hold enough pre-vapor formulation such that the e-vaping device 10 may be configured for vaping for at least about 200 seconds. Moreover, the e-vaping device 10 may be configured to allow each puff to last a maximum of about 5 seconds.

In some example embodiments, the storage medium may be a fibrous material including at least one of cotton, polyethylene, polyester, rayon and combinations thereof. The fibers may have a diameter ranging in size from about 6 microns to about 15 microns (e.g., about 8 microns to about 12 microns or about 9 microns to about 11 microns). The storage medium may be a sintered, porous or foamed material. Also, the fibers may be sized to be irrespirable and may have a cross-section which has a Y-shape, cross shape, clover shape or any other suitable shape. In some example embodiments, the reservoir 95 may include a filled tank lacking any storage medium and containing only pre-vapor formulation.

During a generation of vapor ("an instance of vapor generation"), pre-vapor formulation may be transferred from the reservoir 95 and/or storage medium to the proximity of the heating element 85 via capillary action of the wick 90. The wick 90 may include at least a first end portion and a second end portion, which may extend into opposite sides of the reservoir 95. The heating element 85 may at least partially surround a central portion of the wick 90 such that when the heating element 85 is activated, the pre-vapor formulation in the central portion of the wick 90 may be vaporized by the heating element 85 to form a vapor.

In some example embodiments, the wick 90 may include filaments (or threads) having a capacity to draw the pre-vapor formulation. For example, the wick 90 may be a bundle of glass (or ceramic) filaments, a bundle including a group of windings of glass filaments, etc., all of which arrangements may be capable of drawing pre-vapor formulation via capillary action by interstitial spacings between the filaments. The filaments may be generally aligned in a direction perpendicular (transverse) to the longitudinal direction of the e-vaping device 10. In some example embodiments, the wick 90 may include one to eight filament strands, each strand comprising a plurality of glass filaments twisted together. The end portions of the wick 90 may be flexible and foldable into the confines of the reservoir 95. The filaments may have a cross-section that is generally cross-shaped, clover-shaped, Y-shaped, or in any other suitable shape.

In some example embodiments, the wick 90 may include any suitable material or combination of materials. Examples of suitable materials may be, but not limited to, glass, ceramic- or graphite-based materials. The wick 90 may have any suitable capillarity drawing action to accommodate pre-vapor formulations having different physical properties such as density, viscosity, surface tension and vapor pressure. The wick 90 may be non-conductive.

In some example embodiments, the heating element 85 may include a wire coil ("heater coil") which at least partially surrounds the wick 90. The wire may be a metal wire and/or the heater coil may extend fully or partially along the length of the wick 90. The heater coil may further extend fully or partially around the circumference of the wick 90. In some example embodiments, the heating element 85 may or may not be in contact with the wick 90.

The heating element 85 can be in the form of a wire coil, a planar body, a ceramic body, a single wire, a cage of resistive wire or any other suitable form. The heating element 85 may be any heater that is configured to vaporize a pre-vapor formulation.

In some example embodiments, the heater and/or heater coil may be formed of ("may at least partially comprise") any suitable electrically resistive materials. Examples of suitable electrically resistive materials may include, but not limited to, copper, titanium, zirconium, tantalum and metals from the platinum group. Examples of suitable metal alloys include, but not limited to, stainless steel, nickel, cobalt, chromium, aluminum-titanium-zirconium, hafnium, niobium, molybdenum, tantalum, tungsten, tin, gallium, manganese and iron-containing alloys, and super-alloys based on nickel, iron, cobalt, stainless steel. For example, the heating element 85 may be formed of nickel aluminide, a material with a layer of alumina on the surface, iron aluminide and other composite materials, the electrically resistive material may optionally be embedded in, encapsulated or coated with an insulating material or vice-versa, depending on the kinetics of energy transfer and the external physicochemical properties required. The heating element 85 may include at least one material selected from the group consisting of stainless steel, copper, copper alloys, nickel-chromium alloys, super alloys and combinations thereof. In some example embodiments, the heating element 85 may be formed of nickel-chromium alloys or iron-chromium alloys. In some example embodiments, the heating element 85 may be a ceramic heater having an electrically resistive layer on an outside surface thereof.

The inner tube 70 may include a pair of opposing slots, such that the wick 90 and the first electrical lead 225 and the second electrical lead 225' or ends of the heating element 85 may extend out from the respective opposing slots. The provision of the opposing slots in the inner tube 70 may facilitate placement of the heating element 85 and wick 90 into position within the inner tube 70 without impacting edges of the slots and the coiled section of the heating element 85. Accordingly, edges of the slots may not be allowed to impact and alter the coil spacing of the heating element 85, which would otherwise create potential sources of hotspots. In some example embodiments, the inner tube 70 may have a diameter of about 4 mm and each of the opposing slots may have major and minor dimensions of about 2 mm by about 4 mm.

In some example embodiments, the first lead 225 is physically and electrically connected to the male threaded connector piece 155. As shown, the male threaded first connector piece 155 is a hollow cylinder with male threads on a portion of the outer lateral surface. The connector piece is conductive, and may be formed or coated with a conductive material. The second lead 225' is physically and electrically connected to a first conductive post 130. The first conductive post 130 may be formed of a conductive material (e.g., stainless steel, copper, etc.), and may have a T-shaped cross-section as shown in FIG. 2. The first conductive post 130 nests within the hollow portion of the first connector piece 155, and is electrically insulated from the first connector piece 155 by an insulating shell 135. The first conductive post 130 may be hollow as shown, and the hollow portion may be in fluid communication with the air passage 120. Accordingly, the first connector piece 155 and the first conductive post 130 form respective external electrical connection to the heating element 85.

In some example embodiments, the heating element 85 may heat pre-vapor formulation in the wick 90 by thermal conduction. In some example embodiments, heat from the heating element 85 may be conducted to the pre-vapor formulation by means of a heat conductive element or the heating element 85 may transfer heat to the incoming ambient air that is drawn through the e-vaping device 10 during vaping, which in turn heats the pre-vapor formulation by convection.

It should be appreciated that, instead of using a wick 90, the heating element 85 may include a porous material which incorporates a resistance heater formed of a material having a high electrical resistance capable of generating heat quickly.

As shown in FIG. 2, the second section 20 includes a power supply 145, a control circuit 185 ("control circuitry"), and a sensor 190. As shown, the control circuit 185 and the sensor 190 are disposed in the second housing 30'. A female threaded second connector piece 160 forms a second end. As shown, the second connector piece 160 has a hollow cylinder shape with threading on an inner lateral surface. The inner diameter of the second connector piece 160 matches that of the outer diameter of the first connector piece 155 such that the two connector pieces 155, 160 may be threaded together to form a connection. Furthermore, the second connector piece 160, or at least the other lateral surface is conductive, for example, formed of or including a conductive material. As such, an electrical and physical connection occurs between the first and second connector pieces 155, 160 when connected.

The control circuit 185 may include processing circuity including, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. In some example embodiments, the control circuit 185 may be at least one of an application-specific integrated circuit (ASIC) and an ASIC chip.

As shown, a first lead 165 electrically connects the second connector piece 160 to the control circuit 185. A second lead 170 electrically connects the control circuit 185 to a first terminal 180 of the power supply 145. A third lead 175 electrically connects a second terminal 140 of the power supply 145 to the power terminal of the control circuit 185 to provide power to the control circuit 185. The second terminal 140 of the power supply 145 is also physically and electrically connected to a second conductive post 150. The second conductive post 150 may be formed of a conductive material (e.g., stainless steel, copper, etc.), and may have a T-shaped cross-section as shown in FIG. 2. The second conductive post 150 nests within the hollow portion of the second connector piece 160, and is electrically insulated from the second connector piece 160 by a second insulating shell 215. The second conductive post 150 may also be hollow as shown. When the first and second connector pieces 155, 160 are mated, the second conductive post 150 physically and electrically connects to the first conductive post 130. Also, the hollow portion of the second conductive post 150 may be in fluid communication with the hollow portion of the first conductive post 130.

While the first section 15 has been shown and described as having the male connector piece and the second section 20 has been shown and described as having the female connector piece, some example embodiments include the opposite where the first section 15 has the female connector piece and the second section 20 has the male connector piece.

In some example embodiments, the power supply 145 includes a battery in the e-vaping device 10. The power supply 145 may be a Lithium-ion battery or one of its variants, for example a Lithium-ion polymer battery. In some example embodiments, the power supply 145 may be a nickel-metal hydride battery, a nickel cadmium battery, a lithium-manganese battery, a lithium-cobalt battery or a fuel cell. The e-vaping device 10 may be controlled to generate vapor, based on adult vaper interaction with the e-vaping device 10, until the energy in the power supply 145 is depleted or in the case of lithium polymer battery, a minimum voltage cut-off level is achieved.

In some example embodiments, the power supply 145 is rechargeable. The second section 20 may include circuitry configured to allow the battery to be chargeable by an external charging device. To recharge the e-vaping device 10, an USB charger or other suitable charger assembly may be used as described below.

In some example embodiments, the sensor 190 is configured to generate an output indicative of a magnitude and direction of airflow in the e-vaping device 10. The control circuit 185 receives the output of the sensor 190, and determines if (1) the direction of the airflow indicates a draw on the outlet-end insert 35 and (2) the magnitude of the draw (e.g., a magnitude of the flow rate of the airflow) exceeds a threshold level. If these vaping conditions are met, the control circuit 185 may be understood to have received sensor data, from sensor 190, that amounts to a vapor generation command. In some example embodiments, the e-vaping device 10 includes an interface with which an adult vaper may interact to cause a vapor generation command to be transmitted to the control circuit 185. Based on a determination that a vapor generation command is received at the control circuit 185, the control circuit 185 electrically connects the power supply 145 to the heating element 85; thus, activating the heating element 85. Namely, the control circuit 185 electrically connects the first and second leads 165, 170 (e.g., by activating a heater power control transistor forming part of the control circuit 185) such that the heating element 85 becomes electrically connected to the power supply 145. In some example embodiments, the sensor 190 may indicate a pressure drop, and the control circuit 185 activates the heating element 85 in response thereto.

In some example embodiments, the control circuit 185 may also include a light 60, which the control circuit 185 activates to glow when the heating element 85 is activated and/or the power supply 145 is recharged. The light 60 may include one or more light-emitting diodes (LEDs). The LEDs may include one or more colors (e.g., white, yellow, red, green, blue, etc.). Moreover, the light 60 may be arranged to be visible to an adult vaper during vaping, and may be positioned between the first end 45 and the second end 50 of the e-vaping device 10. In addition, the light 60 may be utilized for e-vaping system diagnostics or to indicate that recharging is in progress. The light 60 may also be configured such that the adult vaper may activate and/or deactivate the heater activation light 60 for privacy.

In some example embodiments, the control circuit 185 may include a time-period limiter. In some example embodiments, the control circuit 185 may include a manually operable switch for an adult vaper to initiate heating. The time-period of the electric current supply to the heating element 85 may be set or pre-set depending on the amount of pre-vapor formulation desired to be vaporized.

Next, operation of the e-vaping device to create a vapor ("vapor generation") will be described. For example, air is drawn primarily into the first section 15 through the at least one air inlet 55 in response to a draw on the outlet-end insert 35. The air passes through the air inlet 55, into the space 250, through the transverse channel 230 into the air passage 235, into the inner passage 120, and through the outlet 100 of the outlet-end insert 35. If the control circuit 185 detects the vaping conditions discussed above (e.g., based on determining that a magnitude of airflow, as indicated by signals ("sensor data") generated by sensor 190 at least meets a threshold level), the control circuit 185 initiates power supply to the heating element 85, such that the heating element 85 heats pre-vapor formulation in the wick 90. The vapor and air flowing through the inner passage 120 combine and exit the e-vaping device 10 via the outlet 100 of the outlet-end insert 35.

When activated, the heating element 85 may heat a portion of the wick 90 for less than about 10 seconds.

In some example embodiments, the first section 15 may be replaceable. In other words, once the pre-vapor formulation of the cartridge is depleted, only the first section 15 may be replaced. In some example embodiments, the entire e-vaping device 10 may be disposed once the reservoir 95 is depleted. In some example embodiments, the e-vaping device 10 may be a one-piece e-vaping device.

In some example embodiments, the e-vaping device 10 may be about 80 mm to about 110 mm long and about 7 mm to about 8 mm in diameter. For example, in some example embodiments, the e-vaping device 10 may be about 84 mm long and may have a diameter of about 7.8 mm.

As shown in FIG. 2, in some example embodiments, a topography apparatus 192 is coupled to the e-vaping device 10 within an interior space 194 of the e-vaping device 10, where the interior space 194 is at least partially defined by housing 30'.

The topography apparatus 192 may generate vapor topography data based on one or more instances of vapor generation by the e-vaping device. In some example embodiments, the topography apparatus 192 may generate vapor topography data based on receiving and/or processing signals generated by one or more elements included within the interior of the e-vaping device 10. Such one or more elements may include one or more elements of the e-vaping device 10 (e.g., control circuit 185, sensor 190, power supply 145, etc.), one or more elements of the topography apparatus 192 (e.g., a sensor included within the topography apparatus 192), some combination thereof, or the like.

As described herein, vapor topography data includes information indicating a physical characteristic of a pattern of vapor generation by the e-vaping device 10. Such a pattern may be associated with a particular adult vaper that may interact with the e-vaping device 10 to cause the e-vaping device 10 to generate vapor according to a particular pattern of vapor generation. As described further below, a particular pattern of vapor generation may include a particular frequency of instances of vapor generation by the e-vaping device 10 over a period of time, a magnitude of an amount and/or flow rate of vapor associated with one or more instances of vapor generation by the e-vaping device 10 over a period of time, some combination thereof, or the like.

Vapor topography data generated by the topography apparatus 192 may include information indicating time stamps at which discrete instances of vapor generation by the e-vaping device 10 occur, information indicating a frequency at which discrete generations of vapor by the e-vaping device 10 occur over a particular time period (e.g., 24 hours, one week, one month, etc.), etc.

Vapor topography data generated by the topography apparatus 192 may include information indicating a determined magnitude of vapor generated by the e-vaping device 10 (e.g., for each discrete instance of vapor generation and/or an average for a particular quantity of vapor generations over a particular period of time), a determined magnitude of a flow rate of air and/or vapor through one or more portions of the e-vaping device 10 concurrently with one or more discrete generations of vapor by the e-vaping device 10, some combination thereof, or the like.

In some example embodiments, vapor topography data may include information indicating a voltage output of a power supply of the e-vaping device in association with generation of vapor by the e-vaping device.

In some example embodiments, vapor topography data may include information indicating a presence and/or amount and/or density of one or more particular volatile organic compounds (VOCs) in a vapor generated by the e-vaping device.

As a result, the vapor topography data may include information indicating a physical characteristic of a pattern of vapor generation by the e-vaping device 10, where such a physical characteristic may include at least one of time stamps at which discrete instances of vapor generation by the e-vaping device 10 occur, a frequency at which discrete generations of vapor by the e-vaping device 10 occur over a particular time period (e.g., 24 hours, one week, one month, etc.), a determined magnitude of vapor generated by the e-vaping device 10 (e.g., for each discrete instance of vapor generation and/or an average for a particular quantity of vapor generations over a particular period of time), a determined magnitude of a flow rate of air and/or vapor through one or more portions of the e-vaping device 10 concurrently with one or more discrete generations of vapor by the e-vaping device 10, a voltage output of a power supply of the e-vaping device in association with generation of vapor by the e-vaping device, a presence and/or amount and/or density of one or more particular volatile organic compounds (VOCs) in a vapor generated by the e-vaping device, some combination thereof, or the like.

In some example embodiments, vapor topography data may include statistical information generated based on processing one or more various signals, received from one or more elements within the interior of the e-vaping device, over a period of time. For example, if and/or when a topography apparatus is configured to generate vapor topography data indicating magnitudes of duration of each instance of vapor generation over a period of time, the topography apparatus may be configured to generate vapor topography data indicating a statistical distribution (e.g., a normal distribution) of vapor generation durations for a given period of time (e.g., a 24-hour period, a week, a month, etc.).

In some example embodiments, vapor topography data includes information associated with one or more signals that are received at the topography apparatus 192 from one or more elements included within the interior of the e-vaping device 10. To generate the vapor topography data, the topography apparatus 192 may simply record the one or more received signals, modify the information included in the signals with one or more instances of metadata (e.g., a timestamp), process the information included in the one or more received signals to generate a new instance of information, some combination thereof, or the like. The one or more signals may each include information indicating at least one of time stamps, a magnitude of vapor generated by the e-vaping device 10 (e.g., for each discrete instance of vapor generation and/or an average for a particular quantity of vapor generations over a particular period of time), a magnitude of a flow rate of air and/or vapor through one or more portions of the e-vaping device 10 concurrently with one or more discrete generations of vapor by the e-vaping device 10, a voltage output of a power supply of the e-vaping device in association with generation of vapor by the e-vaping device, a presence and/or amount and/or density of one or more particular volatile organic compounds (VOCs) in a vapor generated by the e-vaping device, some combination thereof, or the like.

As described further below, the topography apparatus 192 may include an interface assembly that is configured to communicatively couple with one or more elements of the e-vaping device 10 (e.g., the power supply 145, sensor 190, control circuit 185, etc.). The topography apparatus 192 may be configured to receive signals generated by the one or more elements via the interface assembly. As described further below, an interface assembly of the topography apparatus 192 may be configured to couple with pre-existing communication conduits (e.g., electrical leads pins, etc.) of the e-vaping device 10, such that the interface assembly forms branches in the communication conduits and thus "taps in" to the communication conduits to receive signals, generated by one or more elements of the e-vaping device 10, that are then transmitted along the communication conduits. As a result, the interface assembly may enable the topography apparatus 192 to receive signals from one or more elements of the e-vaping device 10 without requiring modification of the e-vaping device 10 to enable the topography apparatus 192 to be coupled thereto to receive such signals.

The topography apparatus 192 may store vapor topography data in a storage device (e.g., a "memory"). As described further below, the topography apparatus may communicate vapor topography data to an external device via a communication interface of the topography apparatus 192.

The topography apparatus 192 may generate control signals based on vapor topography data, where the topography apparatus 192 communicates the control signals to the control circuit 185 of the e-vaping device 10 to control vapor generation by the e-vaping device 10. Restated, the topography apparatus 192 may generate and/or communicate control signals that, when received at the control circuit 185, cause the control circuit 185 to adjustably control vapor generation by the e-vaping device 10. The topography apparatus may generate one or more control signals based on a determination that one or more values associated with generated vapor topography data at least meet one or more threshold values, where a value and/or signal magnitude associated with the control signal is based on a magnitude of the one or more values associated with the generated vapor topography data.

In some example embodiments, the topography apparatus 192 may communicate vapor topography data to that is external to the e-vaping device 10 and the topography apparatus 192 for processing and/or analysis. Such analysis may include generating control signals to be used to control vapor generation operations by the e-vaping device 10. For example, a topography apparatus 192 that communicates vapor topography data to an external device may be configured to receive control signals from the external device, via a communication interface of the topography apparatus 192, such that the topography apparatus 192 may then communicate the received control signals to the control circuit 185 to control vapor generation by the e-vaping device according to the processing and/or analysis of the vapor topography data at the external device.

As described herein, an "external device" may include one or more computing devices ("computers") that may be a centralized device and/or a distributed network of devices. If and/or when an "external device" is a plurality of networked devices, the topography apparatus 192 may be configured to establish a communication link with the plurality of devices via establishing a communication link with at least one computing device of the plurality of networked devices.

The external device may be included in a Data Analytics Ecosystem that is configured to perform analytical functions on the communicated vapor topography data. The external device may be configured to receive and analyze vapor topography data communicated thereto from multiple e-topography apparatuses.

The topography apparatus 192 may communicate with an external device "online" (e.g., concurrently with vapor being generated by the e-vaping device 10) and/or "offline" (e.g., between discrete generations of vapor by the e-vaping device).

Such analysis of the vapor topography data by the external device may enable future product (e.g., cartridge, power supply section, e-vaping device, etc.) improvements, studying of vapor generation "patterns" associated with adult vaper interactions with e-vaping devices, verification of e-vaping device compliance to regulatory requirements, some combination thereof, or the like.

The topography apparatus 192 may include a communication apparatus that includes a wireless network communication interface, such that the topography apparatus 192 is configured to communicate vapor topography data to an external device via a wireless network communication link (e.g., "wireless network connection," "wireless connection," "wireless link," etc.). As a result, the topography apparatus 192 may be configured to enable vapor topography data communication with an external device for processing and/or analysis "transparently" ("invisibly") in relation to an adult vaper interacting with the e-vaping device 10 to cause the e-vaping device 10 to generate vapor. Thus, the effects of coupling a topography apparatus 192 to the e-vaping device 10 may be reduced and/or minimized.

As described herein, vapor topography data generated by a topography apparatus 192 coupled to e-vaping device 10 may enable monitoring of vapor generation patterns associated with the particular e-vaping device 10 and/or an adult vaper that may interact with the particular e-vaping device 10 to cause the e-vaping device 10 to generate vapor according to the vapor generation patterns.

Such monitoring of vapor generation patterns associated with a particular e-vaping device may enable improved control of the e-vaping device 10. For example, in some example embodiments, the generation of vapor by the e-vaping device 10 may be adjustably controlled, based on vapor topography data generated by the topography apparatus 192. The topography apparatus 192 may be communicatively coupled to control circuit 185 and may adjustably control the control circuit 185, to cause the control circuit 185 to adjustably control vapor generation by the e-vaping device 10, based on processing vapor topography data generated by the topography apparatus 192.

As a result of the above, vapor generation by the e-vaping device 10 may be improved and/or optimized to correspond with vapor generation patterns associated with adult vaper interactions with the e-vaping device 10 to cause the e-vaping device 10 to generate vapor.

As a further result, the vapor generation performance of the e-vaping device 10, as perceived by the adult vaper, may be improved as the e-vaping device 10 may generate vapor in closer correspondence with the observed patterns.

In some example embodiments, monitoring of vapor generation patterns associated with a particular e-vaping device 10 may enable improved management of the e-vaping device 10 to maintain vapor generation according to the vapor generation patterns. For example, information indicating a frequency of vapor generation by the e-vaping device 10 (e.g., frequency of instances of vapor generation associated with the e-vaping device 10) that exceeds a particular threshold frequency may be used to present, to an adult vaper that interacts with the e-vaping device 10, information including recommendations to the adult vaper to acquire increased quantities of cartridges (first sections 15) to enable the e-vaping device 10 to maintain the monitored vapor generation frequency.

The e-vaping device 10 may be configured to generate vapor independently of the topography apparatus 192, and the topography apparatus 192 may be configured to enable the e-vaping device 10 to continue generating vapor, concurrently with the topography apparatus 192 being coupled to the e-vaping device 10, without noticeably affecting vapor-generation performance of the e-vaping device 10.

In addition, because the topography apparatus 192 is configured to be coupled to the e-vaping device 10 within an interior space 194 thereof, the topography apparatus 192 may enable an e-vaping device assembly 1 that includes the e-vaping device 10 and the topography apparatus 192 to generate vapor and vapor topography data associated therewith, without noticeably affecting the weight and feel of the e-vaping device 10 (e.g., without changing the total weight of the e-vaping device assembly 1 more than 1%) and further without altering the external appearance of the e-vaping device 10.

In some example embodiments, the topography apparatus 192 includes an interface assembly that is configured to communicatively couple with the power supply 112 such that the topography apparatus 192 consumes power supplied by the power supply to operate. In some example embodiments, the topography apparatus 192 includes a separate power supply that supplies power to one or more elements of the topography apparatus 192 to configure the topography apparatus 192 to operate to generate and/or communicate vapor topography data.

Figure 3B:
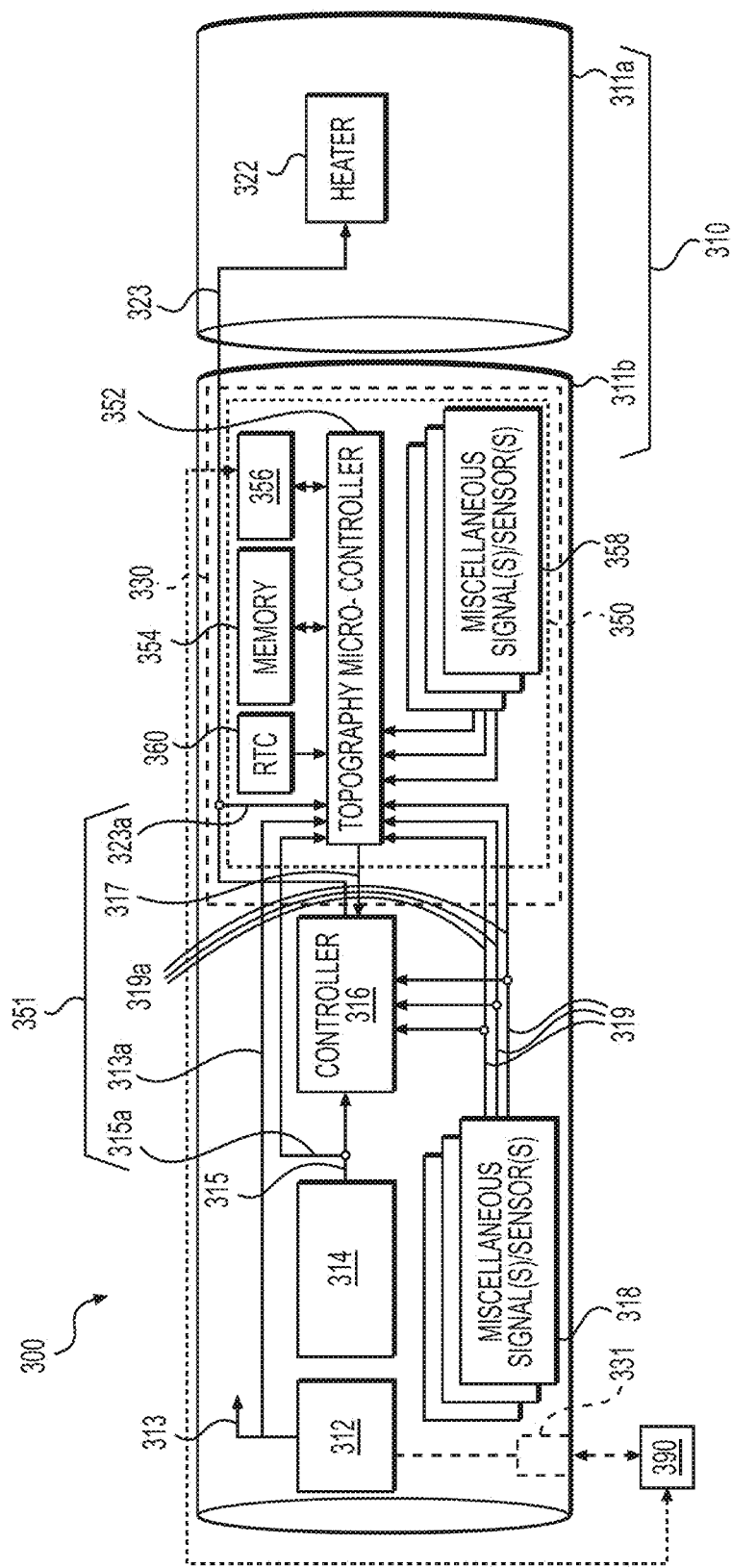
FIG. 3B is a schematic of an e-vaping device in which a topography apparatus is included, according to some example embodiments.

FIG. 3A is a schematic of an e-vaping device assembly 300 that includes an e-vaping device 310 in which a topography apparatus is absent, according to some example embodiments. FIG. 3B is a schematic of an e-vaping device assembly 300 that includes an e-vaping device 310 in which a topography apparatus 350 is included, according to some example embodiments. In some example embodiments, the e-vaping device 310 illustrated in FIGS. 3A-3B may include the e-vaping device 10 shown in FIGS. 1-2. In some example embodiments, the topography apparatus 350 illustrated in FIG. 3B may include the topography apparatus 192 shown in FIG. 2.

As shown in FIGS. 3A-3B, the e-vaping device assembly 300 may include an e-vaping device 310. The e-vaping device assembly 300 may further include a topography apparatus 350 that is coupled to the e-vaping device 310 within an interior space 330 at least partially defined by a housing of the e-vaping device 310. Such a housing may be one or more housings of a housing 301a of the cartridge 311a and a housing 301b of the power supply section 311b The e-vaping device 310 may include a cartridge 311a and a power supply section 311b.

As shown in FIGS. 3A-3B, the cartridge 311a may include a heater 322 that is configured to heat a pre-vapor formulation to generate a vapor, based upon electrical power received at the heater 322 via communication conduit 323.

As shown in FIGS. 3A-3B, the power supply section 311b may include a power supply 312 (e.g., a battery cell or other power source), a sensor 314, and a controller 316 (e.g., "control circuitry," "control circuit," etc.). As further shown in FIGS. 3A-3B, the power supply section 311b may further include one or more additional sensors 318.

The power supply 312 may be coupled to one or more communication conduits 313 via which electrical power may be communicated, as electrical power signals, to one or more of the elements included in the e-vaping device 310.

As described above with reference to FIGS. 1-2, the e-vaping device 310 may include one or more connectors configured to couple the cartridge 311a and power supply section 311b together. Such coupling may result in establishing a communication conduit 323 that communicatively couples the heater 322 to at least the controller 316 and further communicatively couples the heater 322 to the power supply 312. The controller 316 may be configured to control a supply of electrical power from the power supply 312 to the heater 322 via communication conduit 323. Controlling the supply of electrical power to the heater 322 may be referred to herein as the controller 316 generating "control signals" that are communicated to the heater 322 via the communication conduit 323.

In some example embodiments, the controller 316 is configured to automatically control the heater 322 included in the cartridge 311a to control the generation of vapor (instances of vapor generation) by the heater 322. Such control may be implemented by the controller 316 automatically (e.g., without adult vaper intervention) based on a signal received from sensor 314, for example where the sensor 314 is a pressure sensor and/or a flow measuring sensor and where the controller 316. As shown in FIGS. 3A-3B, the power supply section 311b includes a communication conduit 315 that couples sensor 314 with controller 316 to configure the sensor 314 to communicate signals ("sensor data") generated by the sensor 314 to the controller 316. The controller 316 may determine that the signal received from sensor 314 via communication conduit 315 indicates that a magnitude (e.g., flow rate) of air flowing through at least a portion of the e-vaping device 310 at least meets a threshold magnitude. In some example embodiments, the sensor 314 may be included in an interface (e.g., a button, switch, etc.) via which an adult vaper may interact to cause the sensor 314 to generate the signal that, upon being received by the controller 316, prompts the controller 316 to cause the heater 322 to generate vapor.

The controller 316 may be configured to control a supply of electrical power from the power supply 312 to the heater 322 upon receipt ("detection") of the signal from the sensor 314. The controller 316 may be configured to control a supply of electrical power from the power supply 312 to the heater 322 based on processing the signal received from the sensor 314. The controller 316 may be further configured to control charging and/or re-charging of the power supply.

As shown in FIG. 3A and FIG. 3B, in some example embodiments, an e-vaping device 310 may include one or more additional sensors 318. Such one or more additional sensors may include one or more accelerometers configured to detect motions, positions, and/or orientations of the e-vaping device 310 (e.g., gesture sensing and/or monitoring an angle at which the e-vaping device 310 is positioned concurrently with a signal being received at controller 316 by sensor 314, a GPS receiver configured to generate geo-location information, etc. As further shown in FIGS. 3A-3B, the one or more additional sensors 318 may be communicatively coupled to controller 316 via one or more respective communication conduits 319 to configure the one or more additional sensors 318 to communicate signals generated thereby to the controller 316. In some example embodiments, the controller 316 may control the supply of electrical power to heater 322 based on processing signals received from one or more additional sensors 318.

As shown in FIG. 3B, in some example embodiments a topography apparatus 350 is coupled with the e-vaping device 310. As shown in FIG. 3B, the topography apparatus 350 may be coupled to the e-vaping device 310 within the interior space 330 that is at least partially defined by the housing 301b. The topography apparatus 350 is configured to generate vapor topography data based on monitoring and/or receiving signals generated by one or more elements included within the interior of the e-vaping device 310, as at least partially defined by a housing of the e-vaping device 310. The topography apparatus 350 includes a controller 352 (also referred to herein as a "micro-controller," "processor," or the like), a memory 354, a communication interface 356, and one or more topography apparatus sensors 358. As shown in FIG. 3B, in some example embodiments the topography apparatus 350 may include a real-time clock device.

As shown in FIG. 3B, the topography apparatus 350 may include an interface assembly 351 that includes interfaces 313a, 315a, 323a, 319a that are each coupled to separate, respective communication conduits 313, 315, 323, 319. As a result, the topography apparatus 350 is "tapped in" to each of the communication conduits 313, 315, 323, 319, thereby configuring the topography apparatus 350 to receive signals generated by one or more of the elements of the e-vaping device 310 and communicated through one or more of the communication conduits.

For example, as shown in FIG. 3B, the controller 352 is coupled to communication conduit 313 via interface 313a, such that the topography apparatus 350 is configured to receive electrical power signals from the power supply 312. Such electrical power signals may be used to power the topography apparatus 350 and/or may be processed by the controller 352 to monitor vapor generation by the e-vaping device 310 and to generate vapor topography data.

In another example, as shown in FIG. 3B, the controller 352 is coupled to communication conduit 315 via interface 315a, such that the topography apparatus 350 is configured to receive signals generated by the sensor 314, such that the controller 352 may generate vapor topography data based on processing sensor data generated by the sensor 314 and communicated to the e-vaping device controller 316 via communication conduit 315.

In another example, as shown in FIG. 3B, the controller 352 is coupled to communication conduit 319 via interface 319a, such that the topography apparatus 350 is configured to receive signals generated by the one or more additional sensors 318, such that the controller 352 may generate vapor topography data based on processing sensor data generated by the one or more additional sensors 318 and communicated to the e-vaping device controller 316 via communication conduit 319.

In another example, as shown in FIG. 3B, the controller 352 is coupled to communication conduit 323 via interface 323a, such that the topography apparatus 350 is configured to receive control signals (e.g., electrical power) caused to be communicated to the heater 322 by the controller 316, such that the controller 352 may generate vapor topography data based on processing signals caused to be generated by the controller 316 and communicated to the heater 322 via communication conduit 323.

As a result of coupling the topography apparatus 350 to the e-vaping device 310, the e-vaping device assembly 300 is configured to, in addition to generating vapor, generate vapor topography data indicating one or more vapor generation patterns associated with the generation of vapor by the e-vaping device assembly 300.

In some example embodiments, the memory 354 stores at least one program of instructions. The controller 352 may execute the at least one program of instructions to implement one or more elements of vapor topography data generation and/or communication.

In some example embodiments, the controller 352 is communicatively coupled to the e-vaping device controller 316 via one or more interfaces 316a, such that the controller 352 is configured to generate control signals that may be communicated to the controller 316 to cause the controller 316 to adjustably control vapor generation by the heater 322. As a result, the topography apparatus 350 may be configured to, in addition to being a passive "read-only" data measurement and logging system, actively control the operation of the e-vaping device 310.

The topography apparatus 350 (e.g., the controller 352) may determine, based on processing one or more signals (e.g., electrical power signals, control signals, sensor data, etc.) received from one or more elements of the e-vaping device 310, that the e-vaping device 310 is generating vapor according to a particular vapor generation pattern that meets at least one threshold (e.g., a pattern of vapor generation that includes a frequency of instances of vapor generation that at least meets a threshold frequency value and/or pattern of vapor generation that includes a discrete vapor generations having a duration that at least meet a threshold duration value, etc.). Based on such a determination, the topography apparatus 350 may selectively generate a control signal to the controller 316 to cause the controller 316 to adjust the supply of electrical power to the heater 322 (e.g., increase the magnitude of the supplied electrical power to cause the heater 322 to generate a greater mass of vapor during each discrete generation of vapor in response to a signal received from sensor 314.

The topography apparatus 350 may analyze the effects of such adjustable control of the heater 322 (e.g., process sensor data received concurrently with and/or subsequently to generating control signals).

In some example embodiments, the topography apparatus 350 may communicate generated vapor topography data to an external device 390 via communication interface 356, where the external device 390 is separately located in relation to the e-vaping device assembly 300 (e.g., separately located in relation to the e-vaping device 310 and the topography apparatus 350), and the external device 390 may perform analysis of the vapor topography data. The external device 390 may then generate control commands based on such analysis and communicate the control commands to the topography apparatus 350 via communication interface 356. The topography apparatus 350 may then communicate the received control signal to the controller 316 to cause the controller 316 to adjustably control vapor generation by the heater 322. As a result, vapor generation by the e-vaping device 310 may be adjustably controlled based on communication of vapor topography data from the topography apparatus 350 to the external device 390.

As shown in FIG. 3A and FIG. 3B, the topography apparatus 350 may couple with the e-vaping device 310 via connection to pre-existing communication conduits 313, 315, 319 of the e-vaping device 310 without inducing sectioning of the pre-existing communication conduits. For example, as shown in FIG. 3B, the topography apparatus 350 includes an interface assembly that includes interfaces 313a, 315a, 319a that can "tap in" to the pre-existing communication conduits of the e-vaping device 310. As a result, the topography apparatus 350 may be coupled to the e-vaping device 310 without modifying (e.g., "cannibalizing") existing connections, communication conduits, elements of the e-vaping device 310 (e.g., modifying printed PCB boards of the e-vaping device 310 by cutting conductor strips or similar invasive actions).

In some example embodiments, the topography apparatus 350 is configured to tap into (e.g., "sample," "receive," etc.) signals communicated along one or more of the communication conduits of the e-vaping device 310. The topography apparatus 350 may process such signals to determine ("measure") signal values associated with the signals. For example, a signal received from communication conduit 323 via interface 323a may be processed by the topography apparatus 350 to determine a magnitude of electrical power (e.g., a voltage) that is supplied to the heater 322 to cause the heater 322 to generate a vapor.

In another example, a signal received from sensor 314 via communication conduit 315 and interface 315a may be processed by the topography apparatus 350 to determine a magnitude of air flow through the e-vaping device 310.

The topography apparatus 350 may store received and processed signals in the memory 354. The topography apparatus may generate, for each received and processed signal, one or more metadata values that are associated with the signal, including timestamp metadata indicating a timestamp associated with receipt of the signal. For example, where the topography apparatus 350 includes a real time clock device 360, the topography apparatus 350 may be configured to generate a timestamp associated with a determined time at which a signal is received at the topography apparatus 350, and the timestamp may be associated with the signal as a metadata value of the signal. The metadata value associated with a signal may be stored in the memory 354 with the stored signal.

As shown in FIG. 3B, the topography apparatus 350 may include one or more additional sensors 358 that may be configured to provide sensing capabilities that are separate from the capabilities provided by sensors 314, 318. In some example embodiments, the one or more additional sensors 358 may be configured to generate one or more measurements (e.g., "topography sensor data") that are different, in kind and/or in sensitivity, from measurements that may be made by sensors 314, 318. In some example embodiments, the one or more additional sensors 358 are configured to generate signals ("topography sensor data") indicating one or more measurements including air flow rate through at least a portion of the e-vaping device, a temperature of one or more particular portions of an e-vaping device, a pressure (e.g., barometric pressure) at one or more portions of the e-vaping device, a voltage output by a power supply of the e-vaping device, an amount of vapor generated by the e-vaping device, a presence and/or amount and/or density of one or more particular volatile organic compounds (VOCs)

in a vapor generated by the e-vaping device, a time-stamp, some combination thereof, or the like.

In some example embodiments, the one or more additional sensors 358 are configured to generate sensor data associated with measurements of different physical characteristics (e.g., airflow, pressure, voltage, vapor density, vapor generation timestamp and/or duration, vapor composition, etc.) and/or measurements with greater sensitivity than measurements associated with sensor data generated by any of the sensors 314, 318 included in the e-vaping device 310. As a result, the topography apparatus 350 may be configured, based on processing signals received from one or more additional sensors 358, to generate vapor topography data having greater accuracy and/or precision than vapor topography data generated solely based on signals received from one or more sensors 314, 318 of the e-vaping device 310 alone.

In some example embodiments, the topography apparatus 350 includes a communication interface 356 that is configured to communicate vapor topography data generated by the topography apparatus 350 to one or more external devices 390.

In some example embodiments, the communication interface 356 is configured to communicate vapor topography data concurrently with the e-vaping device 310 generating a vapor (such communication is referred to herein as "on-line" communication). Such on-line communication may include communicating the vapor topography data to an external device 390 via a wireless network communication link, such that the vapor topography data is communicated to the external device 390 by the communication interface 356 via a wireless network transmission. Wireless network communication may include communication according to BLUETOOTH® and/or IEEE802.15.4.

In some example embodiments, the communication interface 356 is configured to communicate vapor topography data separately from the e-vaping device 310 generating a vapor (such communication is referred to herein as "off-line" communication). Such off-line communication may include wireless network communication. In some example embodiments, off-line communication may include wired ("hardline") communication with an external device 390 via a communication line coupling the external device 390 and an interface of the e-vaping device (e.g., interface 331).

For example, the topography apparatus 350 may be communicatively coupled to a power charging interface 331 that is configured to enable electrical power to be supplied to the power supply 312 to recharge the power supply. Such an interface 331 may be configured to communicate power and data to or from the e-vaping device 310 and an external device 390. In some example embodiments, the power charging interface 331 may be a Universal Serial Bus (USB) interface. Off-line communication may include communication of vapor topography data to the external device 390 via the power charging interface, based on a determination that the e-vaping device 310 is connected to the external device 390 via the power charging interface. Wireless network communication may include near field communication (NFC). Wireless network communication may include Bluetooth Low Energy (BLE) communication.

In some example embodiments, the e-vaping device 310 may include a communication interface (e.g., a USB interface), and the topography apparatus 350 may be configured to communicate vapor topography data to an external device 390 via a communication conduit (e.g., a USB cable).

In some example embodiments, the topography apparatus 350 is configured to receive signals from one or more elements of the e-vaping device 310, process the received signals, generate vapor topography data, and/or communicate vapor topography data to an external device 390, without consuming sufficient electrical power to noticeably affect vapor generation by the e-vaping device 310. For example, the electrical power consumption by the topography apparatus 350 may be negligible in comparison to the electrical power consumption of the e-vaping device 310. For example, between separate discrete instances of vapor generation by the e-vaping device 310, the electrical power consumption of the topography apparatus 350 may be negligible. In another example, the topography apparatus 350 may be configured to operate in a "sleep mode" between separate discrete instances of vapor generation by the e-vaping device 310.

Figure 4A:
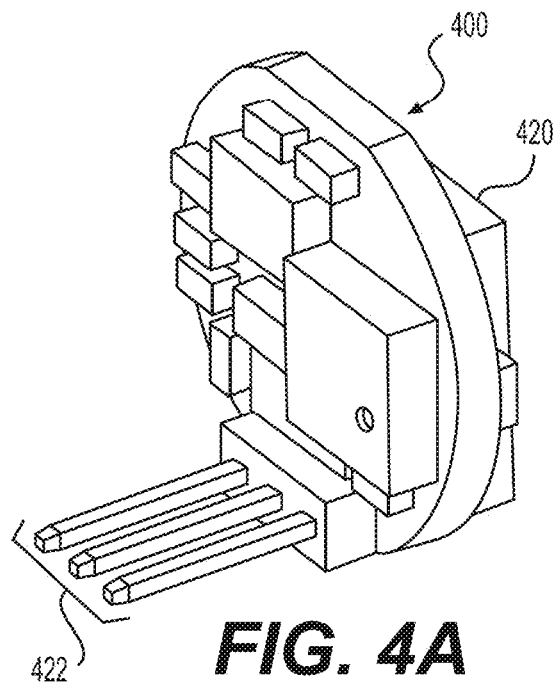
FIG. 4A is a perspective view of a topography apparatus, according to some example embodiments.
Figure 4B:
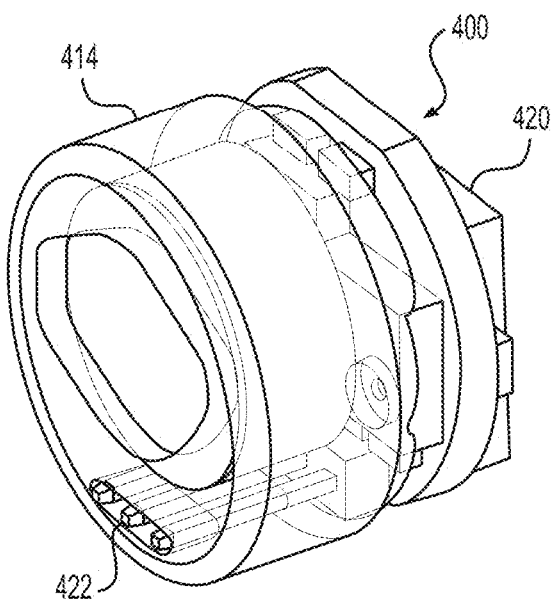
FIG. 4B is a perspective view of a topography apparatus that is coupled to a tip-end portion of an e-vaping device, according to some example embodiments.
Figure 4C:
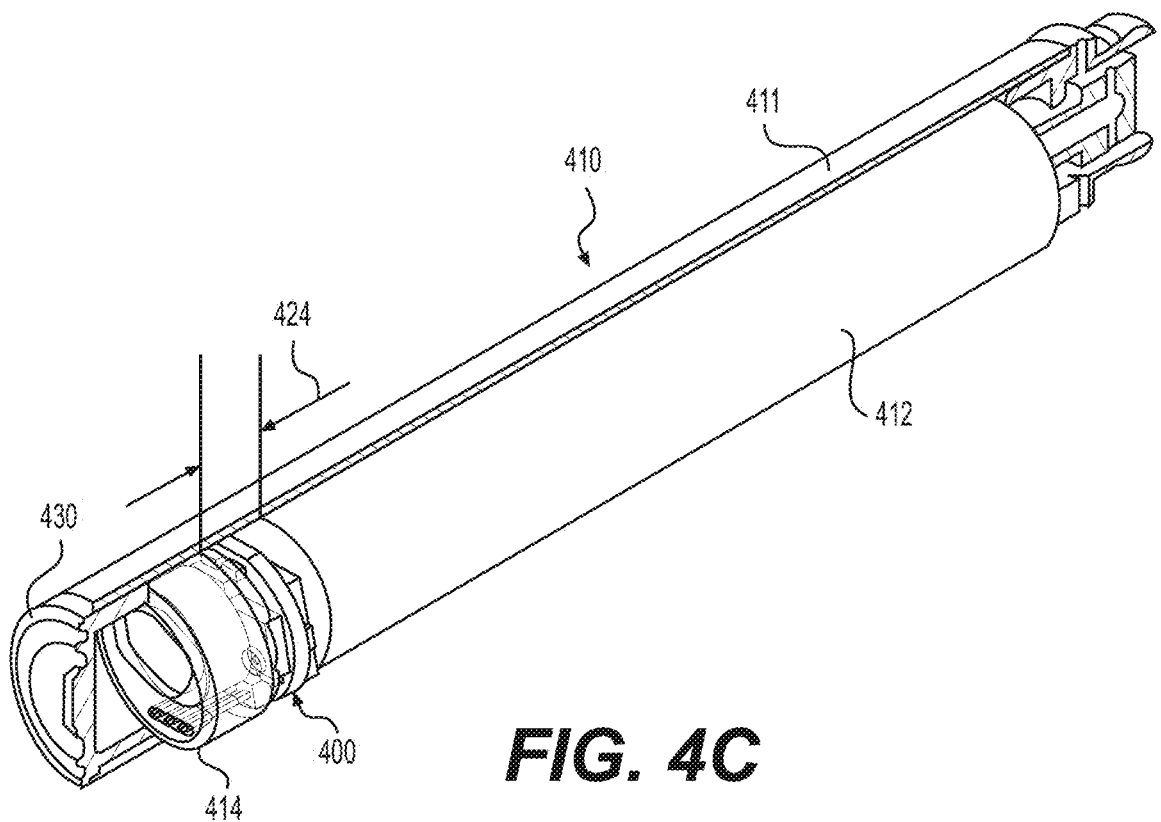
FIG. 4C is a perspective view of a power supply section of an e-vaping device, in which a topography apparatus is included within an interior defined by a housing of the power supply section, according to some example embodiments.
Figure 4D:
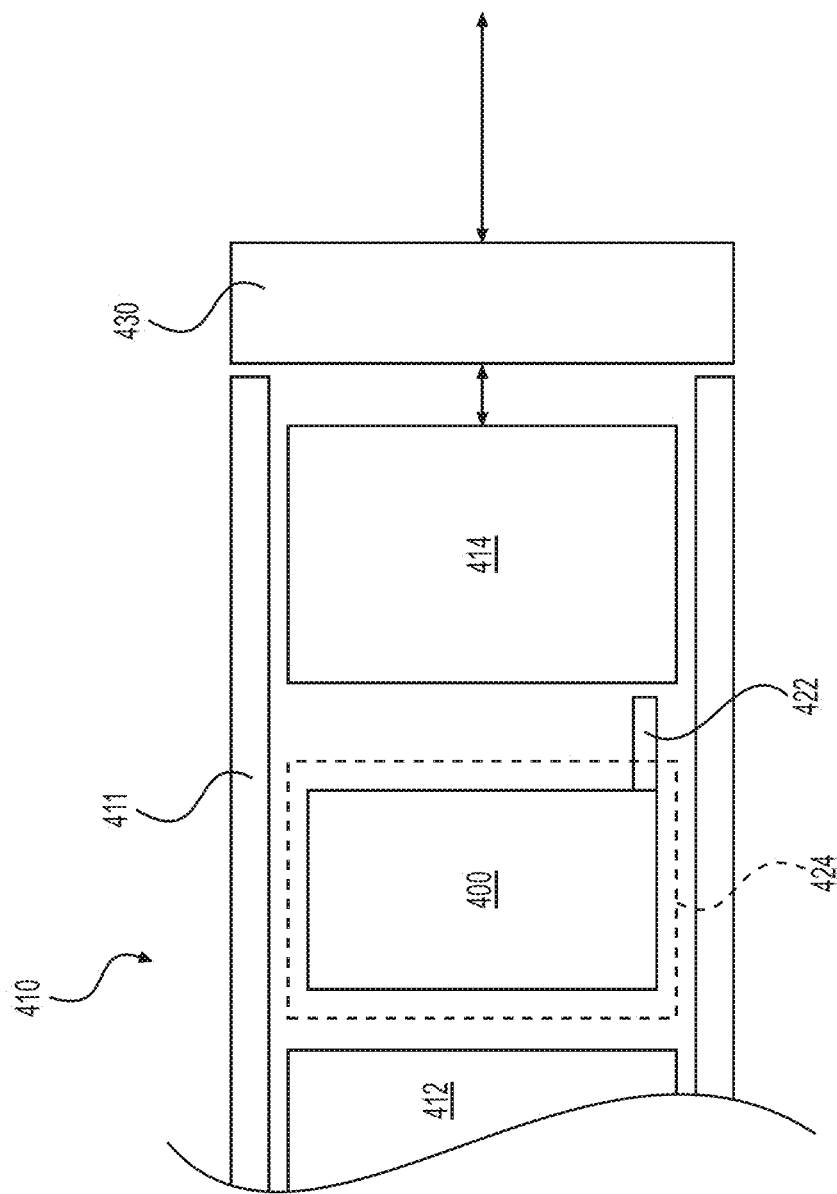
FIG. 4D is a block diagram of a power supply section of an e-vaping device in which a topography apparatus is included, according to some example embodiments.

FIG. 4A is a perspective view of a topography apparatus, according to some example embodiments. FIG. 4B is a perspective view of a topography apparatus that is coupled to a tip-end portion of an e-vaping device, according to some example embodiments. FIG. 4C is a perspective view of a power supply section of an e-vaping device, in which a topography apparatus is included within an interior defined by a housing of the power supply section, according to some example embodiments. FIG. 4D is a block diagram of a power supply section of an e-vaping device in which a topography apparatus is included, according to some example embodiments. The topography apparatus 400 shown in FIGS. 4A-4D may be any of the topography apparatuses included herein, including the topography apparatus 192 shown in FIG. 2.

As shown in FIGS. 4A-4C, a topography apparatus 400 may include an instance of circuitry 420 and an interface assembly 422 that is configured to be communicatively coupled to one or more elements of an e-vaping device. For example, as shown in FIGS. 4B and 4C, the interface assembly 422 may be configured to be coupled to a sensor 414 of the power supply section 410, such that the topography apparatus 400 is communicatively coupled to at least the sensor 414 and thus is configured to receive one or more signals comprising sensor data from the sensor 414.

In some example embodiments, the power supply section 410 of an e-vaping device includes a gap space 424 (e.g., "interior space") that is defined by one or more elements of the power supply section 410. As shown in FIG. 4C, the topography apparatus 400 is configured to be inserted within the gap space 424, such that the topography apparatus 400 is communicatively coupled to the power supply section 410 without affecting the physical configuration ("arrangement") of the elements of the power supply section 410 (e.g., the power supply 412, the sensor 414, etc.).

As shown in FIG. 4C, the topography apparatus 400 may be coupled to at least the power supply section 410 such that the topography apparatus 400 is between the power supply 412 in the power supply section 410 and a sensor 414 in the power supply section 410.

As shown in FIG. 4C and FIG. 4D, the power supply section 410 includes a housing 411, a power supply 412, and a sensor 414 that collectively define an internal space 424 within the power supply section 410. Such an internal space may be a pre-existing internal space of the power supply section 410.

As further shown in FIG. 4C and FIG. 4D, the power supply section 410 includes an end cap 430 that may be detachably coupled to housing 411 to enable reversible access to the interior space 424 of the power supply section 410. The end cap 430 may be located at a tip end of the power supply section 410, and housing 411 may extend along a longitudinal axis of the power supply section 410.

As further shown in FIG. 4D, a topography apparatus 400 may be inserted into the power supply section 410 to be positioned within the interior space 424 thereof. The topography apparatus 400 may be configured to couple to one or more elements of the power supply section 410 from the internal space 424.

As shown in FIG. 4D, the topography apparatus 400 may be configured to be detachably coupled to the power supply section 410 such that the topography apparatus 400 may be removed from the power supply section 410, based on removal of the end cap 430 and removal of the topography apparatus 400 from the power supply section 410 via the opening formed through the removal of the end cap 430.

Figure 5:
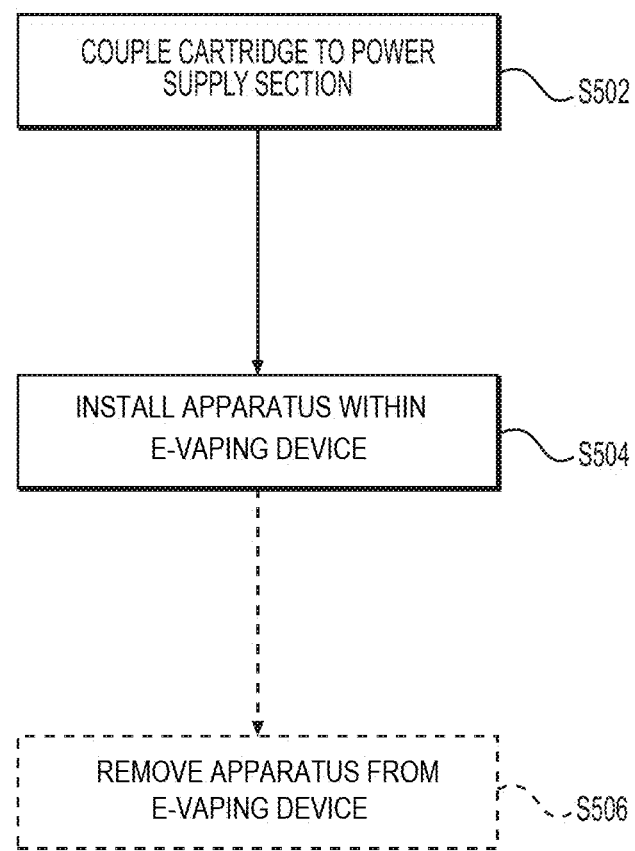
FIG. 5 is a flowchart illustrating configuring an e-vaping device assembly to include a topography apparatus that is coupled to an e-vaping device within an interior space of the e-vaping device, according to some example embodiments.

FIG. 5 is a flowchart illustrating configuring an e-vaping device assembly to include a topography apparatus that is coupled to an e-vaping device within an interior space of the e-vaping device, according to some example embodiments. An e-vaping device assembly described with regard to FIG. 5 may include any of the e-vaping device assemblies described herein, including the e-vaping device assembly 1 shown in FIGS. 1-2, and the e-vaping device assembly 300 shown in FIGS. 3A-3B.

At S502, a cartridge (e.g., first section 15) is coupled to a power supply section (e.g., second section 20) to establish an e-vaping device (e.g., e-vaping device 10). The cartridge and the power supply section may be coupled via one or more connectors (e.g., connectors 25) to enable the power supply section to control a supply of electrical power to a vaporizer assembly of the cartridge to cause the cartridge to generate a vapor. The e-vaping device formed at S502 may be configured to generate vapor without further modification.

At S504, a topography apparatus (e.g., topography apparatus 192) is coupled to the e-vaping device to form an e-vaping device assembly. The topography apparatus may be coupled to the power supply section and/or the cartridge, within an interior space at least partially defined by the housing of at least one section of the power supply section and the cartridge.

Coupling the topography apparatus to the e-vaping device may include communicatively coupling (e.g., electrically coupling) an interface assembly of the topography apparatus to one or more elements of the e-vaping device, such that the topography apparatus is configured to receive one or more signals generated by the one or more elements. Such communicatively coupling may include coupling one or more portions of the interface assembly to one or more communication interfaces and/or communication conduits of the e-vaping device, to configure the topography apparatus to "tap into" said interfaces and/or conduits and receive signals communicated by one or more elements of the e-vaping device through the one or more interfaces and/or conduits.

The topography apparatus may be communicatively coupled (e.g., electrically coupled) to at least the power supply (e.g., rechargeable battery) included in the e-vaping device via an interface assembly of the topography apparatus, such that the topography apparatus may at least receive electrical power from the power supply. The topography apparatus may be configured to monitor electrical power supplied by the power supply to the cartridge in order to generate vapor topography data.

The topography apparatus may be communicatively coupled to a control circuitry, power supply, interface, and/or sensor included in the e-vaping device, via the interface assembly of the topography apparatus, such that the topography apparatus may receive signals generated by the sensor (e.g., "sensor data"), collect data and/or control signals generated by the control circuitry, receive electrical power signals generated by the power supply, receive interface signals generated by the interface, and/or generate control signals that may be communicated to the control circuitry to cause the control circuitry to adjustably control the generation of vapor by the cartridge in response to a vapor-generation command.

The topography apparatus may be coupled to the e-vaping device, within an interior ("interior space") of the e-vaping device as at least partially defined by a housing of the e-vaping device, such that an external appearance of the e-vaping device is not altered by the coupling of the topography apparatus therewith. In addition, the topography apparatus is configured to be coupled to the e-vaping device, without altering the circuitry and/or internal configuration of e-vaping device elements configured to cause vapor to be generated. As a result, the topography apparatus is configured to enable the generation of vapor topography data without noticeably altering the vapor generation functionality ("vapor generation performance") of the e-vaping device.

At S506, the topography apparatus may be decoupled from the e-vaping device, such that the e-vaping device is enabled to continue providing vapor generation functionality in the absence of the topography apparatus. In some example embodiments, the topography apparatus is configured to be detachably coupled to the interior of the e-vaping device, such that the topography apparatus may be decoupled ("detached") from the e-vaping device.

The topography apparatus may then be coupled to a separate e-vaping device to enable the topography apparatus to generate vapor topography data associated with the separate e-vaping device. For example, the topography apparatus may be a temporary apparatus that is configured to be temporarily coupled to a particular e-vaping device to enable the topography apparatus to generate vapor topography data associated with the particular e-vaping device. Upon generation of at least a threshold quantity of such vapor topography data, the topography apparatus may be decoupled from the e-vaping device.

Upon the topography apparatus being decoupled from the e-vaping device, the e-vaping device may be configured to continue generating vapor in response to vapor generation commands, as the vapor-generation functionality of the e-vaping device may not be noticeably affected by the presence or absence of the topography apparatus. Thus, the topography apparatus may enable the generation and/or collection of vapor topography data associated with an e-vaping device without noticeably affecting the vapor generation performance ("functionality") of the e-vaping device.

As a result of such enablement, the topography apparatus may enable the improvement of e-vaping device assemblies that do not include pre-existing topography data generation capability, so that the e-vaping device assemblies are modified by the topography apparatus to enable vapor topography data generation and thus provide the aforementioned benefits associated therewith, without noticeably affecting the pre-existing vapor generation functionality of the e-vaping devices of the e-vaping device assemblies.

Figure 6:
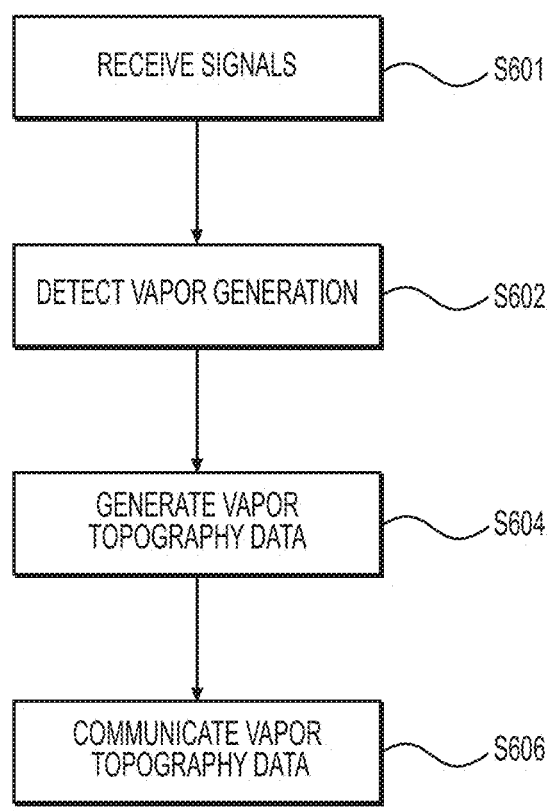
FIG. 6 is a flowchart illustrating topography data-generation operations performed by a topography apparatus, according to some example embodiments.

FIG. 6 is a flowchart illustrating topography data-generation operations performed by a topography apparatus, according to some example embodiments. The operations illustrated in FIG. 6 may be performed by any of the topography apparatuses illustrated and described herein, including the topography apparatus 192 shown in FIG. 2, the topography apparatus 350 shown in FIG. 3B, and the topography apparatus 400 shown in FIGS. 4A-4D.

At S601, the topography apparatus receives one or more signals that are generated by one or more elements within an interior of an e-vaping device to which the topography apparatus is coupled. Such one or more elements may include one or more elements of the e-vaping device to which the topography apparatus is coupled, including a sensor of the e-vaping device, a power supply of the e-vaping device, a control circuit of the e-vaping device, an interface of the e-vaping device, some combination thereof, or the like.

In some example embodiments, where the topography apparatus is communicatively coupled to one or more elements of the e-vaping device via coupling with one or more communication conduits via which the elements of the e-vaping device are configured to communicate ("transmit") signals, the topography apparatus may receive the signals based on "tapping in" to the communication conduits to form a branch in the communication conduits, such that the signals communicated by the one or more elements in the e-vaping device are communicated through the communication conduits and "branch off" to the topography apparatus, in addition to continuing along the communication conduits, to enable the topography apparatus to receive the signals.

If and/or when a signal is received from a sensor, based on an interface assembly of the topography apparatus coupling directly to the sensor or coupling to a communication conduit via which the sensor is configured to communicate signals ("sensor data") to one or more elements of the e-vaping device, including a control circuit of the e-vaping device, the signal may include sensor data generated by the sensor. Such sensor data may include information indicating a measurement of one or more parameters, including air flow rate through at least a portion of the e-vaping device, a temperature of one or more particular portions of an e-vaping device, a pressure (e.g., barometric pressure) at one or more portions of the e-vaping device, a voltage output by a power supply of the e-vaping device, an amount of vapor generated by the e-vaping device, a presence and/or amount and/or density of one or more particular volatile organic compounds (VOCs) in a vapor generated by the e-vaping device, a time-stamp, some combination thereof, or the like.

If and/or when a signal is received from a power supply of the e-vaping device, based on an interface assembly of the topography apparatus coupling directly to the power supply or coupling to a communication conduit via which the power supply is configured to supply electrical power to one or more elements of the e-vaping device, the signal may include a supply of electrical power having one or more particular properties (e.g., voltage, current, etc.). Such a supply of electrical power may be understood to be a signal that includes information indicating the one or more particular properties of power supplied by the power supply to one or more elements of the e-vaping device.

If and/or when a signal is received from a control circuit of the e-vaping device, based on an interface assembly of the topography apparatus coupling directly to the control circuit or coupling to a communication conduit via which the control circuit is configured to communicate signals ("control signals," control circuit-controlled supplies of electrical power to one or more particular elements of the e-vaping device, etc.), the signal may include control signals generated and/or communicated by the control circuit to one or more particular elements of the e-vaping device. Such control signals may include a supply of electrical power, selectively and/or adjustably controlled by the control circuit, to a heating element and/or vaporizer assembly. Such a supply of electrical power may have one or more particular properties that adjustably control the properties of the generated vapor, including a particular magnitude of voltage, current, and/or duration of the control signal. For example, a control signal to generate a relatively large amount of vapor may be a supply of electrical power having a relatively high current. In another example, a control signals to generate vapor over a relatively long duration ("duration of elapsed time") may be a supply of electrical power that is supplied for such a relatively long duration.

At S602, the topography apparatus determines that generation of vapor by an e-vaping device to which the topography apparatus is coupled (e.g., an instance of vapor generation by the e-vaping device) has occurred. Such a determination may be referred to herein as "detecting" the generation of vapor by the e-vaping device.

The topography apparatus may detect the generation of vapor based on processing the one or more signals received at S601. In some example embodiments, the determination at S602 is an optional operation, such that the topography apparatus simply processes received signals as described at S604 below without making a determination of whether an instance of vapor generation has occurred. In some example embodiments, the topography apparatus is configured to generate topography data at S604 based on a determination, at S602, that an instance of vapor generation has occurred.

A determination that an instance of vapor generation has occurred may include processing the one or more signals, received at S601 from one or more elements within the interior of the e-vaping device. Such processing may include determining whether the information included in one or more received signals (e.g., a value of a magnitude of the signal at least meets one or more threshold values.

At S604, the topography apparatus generates vapor topography data based on processing the one or more signals received at S601. As noted above, the generating at S604 may be performed based on a determination, at S604, that an instance of vapor generation by the e-vaping device to which the topography apparatus is coupled has occurred. The topography apparatus may generate topography data based on processing multiple discrete instances of vapor generation by the e-vaping device over one or more periods of time.

Generating vapor topography data may include processing the one or more signals received at S601. Processing a received signal may include storing the signal in a local memory of the topography apparatus. Processing a received signal may include associating the information included in the signal with one or more instances of information included in one or more other received signals. Processing a received signal may include associating the information included in the signal with one or more instances of meta-data (e.g., a time-stamp). Processing one or more received signals may include processing multiple received signals, where the received signals may be received from the same element and/or may be received over a period of time that encompasses multiple instances of vapor generation, to generate statistical data representations of the multiple received signals and/or the multiple instances of vapor generation.

Processing one or more received signals may include associating values, information, etc. included in a signal received from one element within the e-vaping device with values, information, etc. included in a separate signal received from a separate element within the e-vaping device. For example, a pressure value received from a pressure sensor of the e-vaping device may be associated with one or more properties of a control signal generated by the control circuit of the e-vaping device to cause the heating element to generate vapor based on the pressure value.

Signals received from one or more elements may be processed differently to generate vapor topography data, based on processing the signals. For example, pressure data included in a signal received from a sensor of the topography apparatus and control signal property data may be associated with separate, respective timestamps associated with the respective times at which the separate signals are received at the topography apparatus, and the information included in the two, separate signals may be associated with each other to form an instance of vapor topography data based on a determination that the respective timestamps of the separate signals are sufficiently close together (e.g., within a particular threshold common period of elapsed time, e.g., within less than 5 seconds of each other).

At S606, the topography apparatus communicates generated vapor topography data to an external device that is external to the e-vaping device and the topography apparatus. For example, if and/or when the topography apparatus includes a communication interface that is a wireless network communication transceiver, the topography apparatus may communicate (e.g., transmit) the vapor topography data to the external device via wireless network communication. In another example, if and/or when the topography apparatus includes a communication interface that is communicatively coupled to an interface of the e-vaping device (e.g., a USB interface), the topography apparatus may communicate the vapor topography data to the external device via a conduit (e.g., a USB cable) connecting the e-vaping device to the external device via the interface of the e-vaping device.

Example embodiments have been disclosed herein, it should be understood that other variations may be possible. Such variations are not to be regarded as a departure from the spirit and scope of the present disclosure, and all such modifications as would be obvious to one skilled in the art are intended to be included within the scope of the following claims.

What is claimed:

1. A topography apparatus configured to be coupled to an e-vaping device within an interior space that is at least partially defined by a housing of the e-vaping device, the topography apparatus comprising:
    an interface assembly configured to communicatively couple with a power supply of the e-vaping device;
    a memory storing a program of instructions;
    a processor configured to execute the program of instructions to generate vapor topography data based on processing a signal received from an element included within the interior space of the e-vaping device, the vapor topography data indicating a physical characteristic of a pattern of vapor generation by the e-vaping device; and
    a communication interface configured to communicate the vapor topography data to an external device, the external device separately located in relation to the e-vaping device and the topography apparatus,
    wherein the topography apparatus is configured to be detachably coupled with the e-vaping device such that the e-vaping device is configured to generate vapor in an absence of the topography apparatus.

2. The topography apparatus of claim 1, wherein the communication interface is configured to transmit the vapor topography data to the external device via a wireless network connection.

3. The topography apparatus of claim 1, wherein the communication interface is configured to communicatively couple with a power charging interface of the e-vaping device, such that the communication interface is configured to communicate the vapor topography data to the external device via the power charging interface.

4. The topography apparatus of claim 1, further comprising:
    a topography apparatus sensor, the topography apparatus sensor configured to generate topography sensor data based on an operation of the e-vaping device,
    wherein the processor is configured to execute the program of instructions to generate the vapor topography data based on processing the topography sensor data generated by the topography apparatus sensor.

5. The topography apparatus of claim 1, wherein the vapor topography data indicates at least one of
    a time stamp associated with a generation of vapor by the e-vaping device,
    a voltage output of the power supply of the e-vaping device in association with generation of vapor by the e-vaping device,
    an amount of vapor generated by the e-vaping device,
    a flow rate of vapor generated by the e-vaping device, or
    a presence of a volatile organic compound (VOC) in the vapor generated by the e-vaping device.

6. The topography apparatus of claim 1, wherein the interface assembly is configured to couple with a communication conduit of the e-vaping device, the communication conduit communicatively coupling the power supply of the e-vaping device to one or more elements of the e-vaping device, such that the topography apparatus is communicatively coupled to the power supply via the interface assembly and the communication conduit.

7. The topography apparatus of claim 1, wherein the interface assembly is configured to communicatively couple with a control circuitry of the e-vaping device, such that the processor is configured to execute the program of instructions to generate control signals to control the control circuitry based on generating the vapor topography data.

8. An e-vaping device assembly, comprising:
    an e-vaping device configured to generate a vapor, the e-vaping device including
        a vaporizer assembly configured to generate the vapor based on heating a pre-vapor formulation,
        a power supply section configured to supply electrical power to the vaporizer assembly to cause the vaporizer assembly to generate the vapor, the power supply section further including a control circuitry configured to control the supply of electrical power to the vaporizer assembly, and
        a housing encompassing the power supply section; and
    the topography apparatus of claim 1, the topography apparatus coupled with the e-vaping device within an interior space at least partially defined by the housing.

9. The e-vaping device assembly of claim 8, wherein the communication interface is configured to communicatively couple with a power charging interface of the e-vaping device, such that the communication interface is configured to communicate the vapor topography data to the external device via the power charging interface.

10. The e-vaping device assembly of claim 8, the topography apparatus further including
a topography apparatus sensor, the topography apparatus sensor configured to generate topography sensor data based on an operation of the e-vaping device,
wherein the processor is configured to execute the program of instructions to generate the vapor topography data based on processing the topography sensor data generated by the topography apparatus sensor.

11. The e-vaping device assembly of claim 8, wherein the vapor topography data indicates at least one of
a time stamp associated with a generation of vapor by the e-vaping device,
a voltage output of the power supply of the e-vaping device in association with generation of vapor by the e-vaping device,
an amount of vapor generated by the e-vaping device,
a flow rate of vapor generated by the e-vaping device, or
a presence of a volatile organic compound (VOC) in the vapor generated by the e-vaping device.

12. A method, comprising:
coupling a vaporizer assembly to a power supply section to form an e-vaping device configured to generate a vapor; and
coupling a topography apparatus to the e-vaping device within an interior defined by a housing of the e-vaping device, such that
the e-vaping device is configured to generate the vapor independently of the topography apparatus, and
the topography apparatus is configured to generate vapor topography data associated with the e-vaping device, the vapor topography data indicating a physical characteristic of a pattern of vapor generation by the e-vaping device, the topography apparatus further configured to communicate the vapor topography data to an external device, the external device separately located in relation to the e-vaping device and the topography apparatus, wherein,
the topography apparatus is configured to be detachably coupled to the interior of the e-vaping device, and
the method further includes decoupling the topography apparatus from the e-vaping device such that the e-vaping device is configured to generate vapor in an absence of the topography apparatus.

13. The method of claim 12, wherein the topography apparatus includes a topography apparatus sensor, the topography apparatus sensor configured to generate topography sensor data based on an operation of the e-vaping device, the topography apparatus further configured to generate the vapor topography data based on processing sensor data generated by the topography apparatus sensor.

14. The method of claim 12, wherein the vapor topography data indicates at least one of
a time stamp associated with a generation of vapor by the e-vaping device,
a voltage output of a power supply of the e-vaping device in association with generation of vapor by the e-vaping device,
an amount of vapor generated by the e-vaping device,
a flow rate of vapor generated by the e-vaping device, or
a presence of a volatile organic compound (VOC) in the vapor generated by the e-vaping device.

15. A method, comprising:
receiving, at a topography apparatus coupled to an e-vaping device within an interior defined by a housing of the e-vaping device, a signal from an element included within the interior of the e-vaping device, the signal being received based on a generation of vapor by the e-vaping device;
generating vapor topography data based on processing the signal, the vapor topography data indicating a physical characteristic of a pattern of vapor generation by the e-vaping device; and
communicating the vapor topography data to an external device, the external device separately located in relation to the e-vaping device and the topography apparatus,
wherein the topography apparatus is configured to be detachably coupled with the e-vaping device such that the e-vaping device is configured to generate vapor in an absence of the topography apparatus.

16. The method of claim 15, wherein the vapor topography data indicates at least one of
a time stamp associated with the generation of vapor by the e-vaping device,
a voltage output of a power supply of the e-vaping device in association with generation of vapor by the e-vaping device,
an amount of vapor generated by the e-vaping device,
a flow rate of vapor generated by the e-vaping device, or
a presence of a volatile organic compound (VOC) in the vapor generated by the e-vaping device.

17. The method of claim 15, wherein the communicating includes transmitting the vapor topography data to the external device via a wireless network connection.

* * * * *